(12) United States Patent
Kahlman et al.

(10) Patent No.: US 10,201,299 B2
(45) Date of Patent: Feb. 12, 2019

(54) REDUCING NON-REVERSIBLE CROSS SENSITIVITY FOR VOLATILE ACIDS OR BASES IN CHEMO-OPTICAL SENSOR SPOTS

(71) Applicant: KONINKLIJKE PHILIPS N.V., Eindhoven (NL)

(72) Inventors: Josephus Arnoldus Henricus Maria Kahlman, Tilburg (NL); Nicolaas Lambert, Waalre (NL); Hans Willem Van Kesteren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 344 days.

(21) Appl. No.: 15/109,826

(22) PCT Filed: Dec. 23, 2014

(86) PCT No.: PCT/EP2014/079105
§ 371 (c)(1),
(2) Date: Jul. 6, 2016

(87) PCT Pub. No.: WO2015/104184
PCT Pub. Date: Jul. 16, 2015

(65) Prior Publication Data
US 2016/0331289 A1    Nov. 17, 2016

(30) Foreign Application Priority Data
Jan. 7, 2014    (EP) .................................. 14150298

(51) Int. Cl.
*A61B 5/1455*    (2006.01)
*G01N 21/78*    (2006.01)
(Continued)

(52) U.S. Cl.
CPC ........ *A61B 5/14556* (2013.01); *A61B 5/0059* (2013.01); *A61B 5/01* (2013.01);
(Continued)

(58) Field of Classification Search
CPC .............. A61B 5/1477; A61B 5/14552; A61B 5/14556; A61B 5/1491; A61B 5/0059; A61B 5/01; A61B 5/443; A61B 5/783
See application file for complete search history.

(56) References Cited

U.S. PATENT DOCUMENTS 4,003,707 A * 1/1977 Lubbers ............... G01N 21/643
356/318
4,041,932 A * 8/1977 Fostick .............. A61B 5/14539
356/39

(Continued)

FOREIGN PATENT DOCUMENTS

CN    1946998 A    4/2007
EP    1965198 A1    9/2008
(Continued)

OTHER PUBLICATIONS

Schaferling: "The Art of Fluorescence Imaging With Chemical Sensors"; Angewandte Chemi International Edition, vol. 51, Issue 15, Apr. 2012, pp. 3532-3554.

*Primary Examiner* — Eric Winakur
*Assistant Examiner* — Chu Chuan Liu

(57) ABSTRACT

The present invention relates to a chemo-optical sensor unit for transcutaneous measurement of a concentration of a gas, comprising: at least one gas-permeable sensing layer adapted to be irradiated with a predetermined radiation; and at least a first gas-permeable layer adjacent to one side of the at least one sensing layer, adapted to pass gas whose concentration is to be measured through the gas-permeable layer towards the sensing layer; at least one volatile acid and/or base binding layer in the gas-pathway from the skin (Continued)

to the sensing layer; adapted to pass gas whose concentration is to be measured through the volatile acid and/or base binding layer towards the sensing layer; wherein said chemo-optical sensor unit is adapted to operate with a contact medium between the chemo-optical sensor unit and the skin and wherein the chemo-optical sensor unit is adapted to measure an optical response of the at least one sensing layer, whose optical response depends on the concentration of the gas. The present invention also relates to a system for patient monitoring and/or ventilation of a patient comprising such a chemo-optical sensor.

15 Claims, 6 Drawing Sheets

(51) Int. Cl.
    *A61B 5/00*     (2006.01)
    *A61B 5/01*     (2006.01)
    *A61B 5/1477*     (2006.01)
    *A61B 5/1491*     (2006.01)
    *G01N 21/77*     (2006.01)

(52) U.S. Cl.
    CPC .......... *A61B 5/1477* (2013.01); *A61B 5/1491* (2013.01); *A61B 5/14552* (2013.01); *A61B 5/443* (2013.01); *G01N 21/783* (2013.01); *G01N 2021/773* (2013.01); *G01N 2021/7786* (2013.01)

(56) References Cited

U.S. PATENT DOCUMENTS

| | | | |
|---|---|---|---|
| 2001/0034479 A1* | 10/2001 | Ring | A61B 5/14556 600/322 |
| 2003/0003593 A1 | 1/2003 | Wallach | |
| 2007/0078318 A1 | 4/2007 | Kling et al. | |
| 2009/0004751 A1* | 1/2009 | Leiner | G01N 21/783 436/133 |
| 2010/0136607 A1 | 6/2010 | Upreti et al. | |
| 2010/0178203 A1* | 7/2010 | Kane | A61B 5/1455 435/29 |

FOREIGN PATENT DOCUMENTS

| | | |
|---|---|---|
| WO | 02056023 A1 | 7/2002 |
| WO | 2005095924 A1 | 10/2005 |
| WO | 2008013849 A2 | 1/2008 |

* cited by examiner

REDUCING NON-REVERSIBLE CROSS SENSITIVITY FOR VOLATILE ACIDS OR BASES IN CHEMO-OPTICAL SENSOR SPOTS

CROSS-REFERENCE TO PRIOR APPLICATIONS

This application is the U.S. National Phase application under 35 U.S.C. § 371 of International Application No. PCT/EP2014/079105, filed on Dec. 23, 2014, which claims the benefit of or European Patent Application No. 14150298.9, filed on Jan. 7, 2014. These applications are hereby incorporated by reference herein.

FIELD OF THE INVENTION

The present invention relates to a chemo-optical sensor unit for transcutaneous measurement of a concentration of a gas, comprising: at least one gas-permeable sensing layer adapted to be irradiated with a predetermined radiation; and at least a first gas-permeable layer adjacent to one side of the at least one sensing layer, adapted to pass gas whose concentration is to be measured through the gas-permeable layer towards the sensing layer; at least one volatile acid and/or base binding layer in the gas-pathway from the skin to the sensing layer; adapted to pass gas whose concentration is to be measured through the volatile acid and/or base binding layer towards the sensing layer; wherein said chemo-optical sensor unit is adapted to operate with a contact medium between the chemo-optical sensor unit and the skin and wherein the chemo-optical sensor unit is adapted to measure an optical response of the at least one sensing layer, whose optical response depends on the concentration of the gas. The present invention also relates to a system for patient monitoring and/or ventilation of a patient comprising such a chemo-optical sensor.

BACKGROUND OF THE INVENTION

Neuromuscular disease, chronic obstructive pulmonary disease (COPD) and obese hypoventilation patients often suffer from chronic respiratory failure. Said patients need regular treatment of their respiratory failure at home. Hypoxemic patients are treated by oxygen therapy (mostly without ventilator support), while treatment by Invasive Ventilation (IV) and Non Invasive Ventilation (NIV) with environmental air helps bringing the high carbon dioxide ($CO_2$) blood gas level of hypercapnic patients back to an acceptable level. The efficacy of the ventilation is checked by measuring the base-line and the trends in the arterial oxygen and carbon dioxide levels during nocturnal NIV.

Arterial blood gas measurements form the golden standard. Before starting ventilation treatment at home, patients stay at the hospital to optimize ventilator settings and monitor arterial blood gas values. Depending on disease severity and stability, patients have to return more or less regularly to the hospital for checks. A respiratory nurse can also visit the patient at home to check the ventilator and to install equipment that enables non-invasive monitoring of blood gas partial pressures. At home, blood gas levels are monitored typically during a night and data are stored together with ventilator and respiratory data for later analysis at the hospital.

The state of the art in non-invasive blood oxygenation monitoring, is by measuring the arterial oxygen saturation, which relates to the partial oxygen pressure via the oxygen dissociation curve. Pulse oximetry ($SpO_2$) is an optical method for non-invasive monitoring of arterial oxygen saturation in a patient and has become one of the most commonly used technologies in clinical practice. Pulse oximetry is a reasonably low cost technology and is easy to use. It is the preferred method for blood oxygenation monitoring at home.

The state of the art in non-invasive monitoring of the partial pressure of $CO_2$ is by means of capnography or by transcutaneous $CO_2$ ($PtcCO_2$) monitoring. For intubated patients with a healthy lung the end tidal $CO_2$ ($etCO_2$) value obtained by capnography offers a good indication of the arterial $CO_2$ value. However, in case of non-invasive ventilation where air leaks between mask and face are usually present and the patients have severe respiratory diseases capnography is often not a reliable method. In most hospitals a combination is used of capnography for trend monitoring and analysis of an arterial blood sample to obtain an occasional accurate value.

Transcutaneous $CO_2$ monitoring is not disrupted by airleaks and respiratory diseases but requires trained personal to obtain reliable values and shows some inaccuracy due to variation in skin properties among adults. At home $CO_2$ blood gas monitoring is less frequently used than oximetry despite its high relevance for patients receiving ventilation.

Current transcutaneous $CO_2$ sensors are all based on a 40 year old concept of (i) a thermostatically controlled heater to increase blood perfusion and gas-permeability of the skin; (ii) a fluid layer between skin and sensor membrane; (iii) a gas-permeable membrane covering the sensor; (iv) an electrolyte solution between membrane and sensor; (v) a sensor comprising an electrochemical pH sensor and reference electrode; and (v) an algorithm to compensate for temperature effects and skin metabolism.

EP 1 965 198 A1 describes a device for determining $CO_2$ in gaseous or liquid samples comprising a polymer matrix and an indicator embedded in the polymer matrix, wherein the indicator comprises a pH sensitive dye and a metal cation complex, wherein an anion of the pH-sensitive dye and the metal cation form a salt which is soluble in the polymer matrix.

A further example of a prior art chemo-optical sensor for transcutaneous application is depicted in FIG. 1, wherein on top of an optical transparent carrier material two layers of 'silicon rubber-like' gas-permeable materials are deposited. The first layer—the sensing layer—comprises a mixture of two luminescent dyes within a hydrophobic polymer, namely a reference dye having a long luminescent life-time and a pH-sensitive indicator dye having a short luminescent life-time. A second membrane layer comprises light reflecting material ($TiO_2$) particles and prevents ion transport to and from the sensing layer. $CO_2$ gas typically diffuses through said membrane into the first (sensing) layer and changes the pH, which in turn modifies the luminescence from the indicator dye. By using a dual life-time referencing technique, which effectively measures the time response of modulated light excitation, the percentage of $CO_2$ gas can be calculated.

The chemo-optical sensors are, however, cross sensitive with respect to volatile acids and/or bases. The human skin produces different molecules, including acids such as acetic acids as a result of the metabolism of bacteria on the skin, or as result of medications or diseases, or bases such as ammonia as result of sweating or due to kidney diseases or diabetes. Further sources of volatile acids is smoke, e.g. in environments in which the chemo-optical sensor are stored. Volatile acids such as acetic acid, HCl and $SO_2$ vapors, or volatile bases such as ammonium, derived from the skin or the environment or package during storage may enter the chemo-optical sensor, introduce a non-reversible drift within the sensor and accordingly deteriorate the sensor response.

In consequence, there is a need for the development of an improved chemo-optical sensor for transcutaneous applications, in which the effect of volatile acids or bases on the functioning of the sensor is reduced, counterbalanced or compensated.

OBJECTS AND SUMMARY OF THE INVENTION

The present invention addresses these needs and provides means and methods for reducing non-reversible cross sensitivity for volatile acids or bases in chemo-optical sensor spots. The above objective is in particular accomplished by a chemo-optical sensor unit for transcutaneous measurement of a concentration of a gas, comprising: at least one gas-permeable sensing layer adapted to be irradiated with a predetermined radiation; and at least a first gas-permeable layer adjacent to one side of the at least one sensing layer, adapted to pass gas whose concentration is to be measured through the gas-permeable layer towards the sensing layer; at least one volatile acid and/or base binding layer in the gas-pathway from the skin to the sensing layer, adapted to pass gas whose concentration is to be measured through the volatile acid and/or base binding layer towards the sensing layer; wherein said chemo-optical sensor unit is adapted to operate with a contact medium between the chemo-optical sensor unit and the skin and wherein the chemo-optical sensor unit is adapted to measure an optical response of the at least one sensing layer, whose optical response depends on the concentration of the gas. In particular, it was surprisingly found by the inventors that at least one volatile acid and/or base binding layer in the gas-pathway from the skin to the sensing layer allows to reduce or avoid the effect of volatile acids or bases on the functioning of the sensor. The volatile acid and/or base binding layer was accordingly found to bind the unwanted volatile acids or bases and/or to convert them into non-volatile molecules, which cease to deteriorate the sensor response. The use of such binding layers further provides the advantage that it is largely compatible with current fabrication process, e.g. due to the use of the same or similar materials, or the employment of the same or similar deposition techniques. Further, their simple form and structure does not contribute to the addition of further complexity to the sensor device. Moreover, there is no impact on the optical detection method, since the additional layer is located outside of the optical pathway.

One embodiment of the present invention relates to a chemo-optical sensor unit for transcutaneous measurement of a concentration of a gas, comprising: at least one gas-permeable sensing layer adapted to be irradiated with a predetermined radiation; and at least a first gas-permeable layer adjacent to one side of the at least one sensing layer, adapted to pass gas whose concentration is to be measured through the gas-permeable layer towards the sensing layer; at least one volatile acid and/or base binding layer in the gas-pathway from the skin to the sensing layer, adapted to pass gas whose concentration is to be measured through the volatile acid and/or base binding layer towards the sensing layer; wherein said chemo-optical sensor unit is adapted to operate with a contact medium between the chemo-optical sensor unit and the skin and wherein the chemo-optical sensor unit is adapted to measure an optical response of the at least one sensing layer, whose optical response depends on the concentration of the gas, wherein the at least one gas-permeable layer and the at least one one gas-permeable sensing layer are distinct layers.

One embodiment of the present invention relates to a chemo-optical sensor unit for transcutaneous measurement of a concentration of a gas, comprising: at least one gas-permeable sensing layer adapted to be irradiated with a predetermined radiation; and at least a first gas-permeable layer adjacent to one side of the at least one sensing layer, adapted to pass gas whose concentration is to be measured through the gas-permeable layer towards the sensing layer; at least one volatile acid and/or base binding layer in the gas-pathway from the skin to the sensing layer, adapted to pass gas whose concentration is to be measured through the volatile acid and/or base binding layer towards the sensing layer; wherein said chemo-optical sensor unit is adapted to operate with a contact medium between the chemo-optical sensor unit and the skin and wherein the chemo-optical sensor unit is adapted to measure an optical response of the at least one sensing layer, whose optical response depends on the concentration of the gas, wherein there is at least one gas-permeable layer between the at least one gas-permeable sensing layer and the at least one volatile acid and/or base binding layer.

One embodiment of the present invention relates to a chemo-optical sensor unit for transcutaneous measurement of a concentration of a gas, comprising: at least one gas-permeable sensing layer adapted to be irradiated with a predetermined radiation; and at least a first gas-permeable layer adjacent to one side of the at least one sensing layer, adapted to pass gas whose concentration is to be measured through the gas-permeable layer towards the sensing layer; at least one volatile acid and/or base binding layer adjacent to the at least first gas-permeable layer, in the gas-pathway from the skin to the sensing layer, adapted to pass gas whose concentration is to be measured through the volatile acid and/or base binding layer towards the sensing layer; wherein said chemo-optical sensor unit is adapted to operate with a contact medium between the chemo-optical sensor unit and the skin and wherein the chemo-optical sensor unit is adapted to measure an optical response of the at least one sensing layer, whose optical response depends on the concentration of the gas.

In a preferred embodiment of the present invention the at least one volatile acid and/or base binding layer comprises at least one compound capable of binding a volatile acid and/or base, preferably capable of immobilizing said volatile acid(s) or volatile base(s) or of converting said volatile acid(s) or volatile base(s) into non-volatile molecules and/or of converting said volatile acid(s) into less acidic volatile molecules and/or said volatile base(s) into less alkaline volatile molecules.

In a further preferred embodiment the at least one volatile acid and/or base binding layer has a non-continuous structure allowing the contact medium to directly contact the at least one gas-permeable layer at one or more positions.

In yet another preferred embodiment said non-continuous structure is a single or multiple sequences of blocks of volatile acid and/or base binding layer followed by single or multiple gaps.

In another preferred embodiment of the present invention, said at least one volatile acid binding layer is capable of attracting and binding 70%, 80%, 90%, 95%, 96%, 97%, 98%, 99% or more of the volatile acids and/or volatile bases entering the chemo-optical sensor unit during the period of transcutaneous measurement and/or during the period of storage of the chemo-optical sensor before usage.

In yet another preferred embodiment of the present invention, the chemo-optical sensor unit additionally comprising at least a further, second gas-permeable layer adjacent to one side of the at least one volatile acid and/or base binding layer or to one side of the first gas-permeable layer, adapted to pass gas whose concentration is to be measured towards the sensing layer and further adapted to prevent ions to pass from the chemo-optical sensor unit to the skin, or from the skin into the chemo-optical sensor unit.

In a further embodiment of the present invention said further, second gas-permeable layer and/or said contact medium comprises an ion-balancing means capable of removing the ions associated with volatile acids and/or bases.

In a further preferred embodiment, said ion-balancing means is an ion-trapping means, an ion-exchange polymer, an ion-exchange resin, preferably an anion-exchange resin or any combination thereof.

In another preferred embodiment, said at least one compound capable of binding or converting a volatile acid or base is a chemical buffer, preferably a phosphate buffer.

In an additional embodiment of the present invention, which is also preferred, said at least one volatile acid and/or base binding layer has a thickness of about 10% to about 300% of the thickness of the at least one sensing layer or of the at least one gas-permeable layer.

In a further preferred embodiment of the present invention said at least one gas-permeable layer and/or said at least one sensing layer and/or said at least one volatile acid and/or base binding layer comprises a silicon rubber.

In another preferred embodiment of the present invention said at least one sensing layer comprises luminescent material. In yet another preferred embodiment, additionally said volatile acid and/or base binding layer comprises luminescent material. In yet another embodiment of the present invention, said first gas-permeable layer is adapted to prevent light from passing through the gas-permeable layer.

In a further preferred embodiment of the present invention the chemo-optical sensor unit is a transcutaneous sensor unit for measuring blood gas concentration. It is particularly preferred that the chemo-optical sensor unit is for measuring the blood gas concentrations of $O_2$ or $CO_2$ or simultaneously $O_2$ and $CO_2$. In a more preferred embodiment, the chemo-optical sensor unit is for measuring the blood gas concentration of $CO_2$.

In a further embodiment the chemo-optical sensor unit as defined herein above further comprises: at least one light source adapted to irradiate the sensing layer, and optionally a light guiding structure connected to the light source; and at least one detection device adapted to detect the optical response of the sensing layer, and optionally a light guiding structure connected to the detection device. In a preferred embodiment, at least one of the light source, light guiding structure and/or the detection device are detachably connected to the chemo-optical sensor unit.

In a further aspect, the present invention relates to a system for patient monitoring and/or ventilation of a patient, comprising a chemo-optical sensor unit as defined herein above, a ventilation device and/or a monitoring device.

DETAILED DESCRIPTION OF THE EMBODIMENTS

Figure 1:
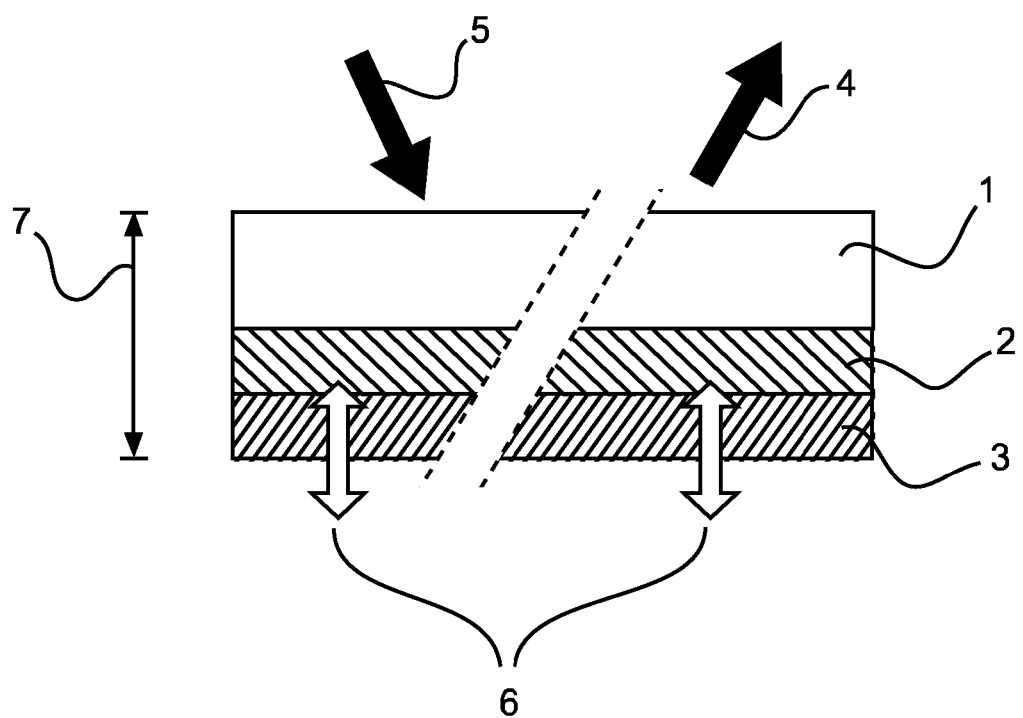
FIG. 1 shows the principles of a chemo-optical sensor for transcutaneous application. The figure depicts a chemo-optical sensor comprising a support layer, a sensing layer, as well as a layer which is transparent to gas and reflective to light.

The present invention relates to a chemo-optical sensor unit for transcutaneous measurement of a concentration of a gas comprising at least one volatile acid and/or base binding layer in the gas-pathway from the skin to the sensing layer.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a chemo-optical sensor unit for transcutaneous measurement of a concentration of a gas, comprising: at least one gas-permeable sensing layer adapted to be irradiated with a predetermined radiation; and at least a first gas-permeable layer adjacent to one side of the at least one sensing layer, adapted to pass gas whose concentration is to be measured through the gas-permeable layer towards the sensing layer; at least one volatile acid and/or base binding layer in the gas-pathway from the skin to the sensing layer, adapted to pass gas whose concentration is to be measured through the volatile acid and/or base binding layer towards the sensing layer; wherein said chemo-optical sensor unit is adapted to operate with a contact medium between the chemo-optical sensor unit and the skin and wherein the chemo-optical sensor unit is adapted to measure an optical response of the at least one sensing layer, whose optical response depends on the concentration of the gas.

The term "concentration of a gas" relates to the amount of gas arriving at the chemo-optical sensor due to diffusion from zones or sectors to be measured. A "gas" may be any gaseous material. It is preferred that the gas is a biologically produced or biologically active or relevant gas. Examples of such gases are $O_2$, $CO_2$, CO, $N_2$, $NH_3$, NO, $H_2S$. It is preferred that the gas whose concentration should be measured is $O_2$ and/or $CO_2$. Also envisaged is the simultaneous measurement of $O_2$ and $CO_2$, or any other combination of gases mentioned above. It is particularly preferred that the gas whose concentration should be measured is $CO_2$.

The term "sensing layer" as used herein refers to a layer which may be irradiated or excited and which may subsequently generate a light of a different wavelength due to the excitation of an optically reactive material, e.g. luminescence such as fluorescence, as optical response, wherein the intensity of the generated light depends on the concentration of gas molecules present in or dissolved in the sensing layer. The measurement of the optical response, e.g. luminescence such as fluorescence, of a certain intensity and wavelength, allows to calculate the gas concentration in the sensing layer, e.g. being diffusing or having diffused into the sensing layer from deeper layers such as the skin. This measurement may further allow a calculation of the concentration of such gas in the sector to be measured, e.g. in the sector of the skin on which the chemo-optical sensor is placed.

The sensing layer may be composed of filler material which is passable for gas molecules. An example of such filler material is silicone rubber material. In a preferred embodiment, the sensing layer may thus comprise silicone rubber or essentially consist of silicon rubber material. The sensing layer may further comprise compounds such as water or chemical buffers. The sensing layer may accordingly be buffered at a specific pH or comprise a certain amount of protons and/or hydroxide ions, e.g. have a certain pH. The pH which may be changed due to the diffusion of gases, in particular $CO_2$ into the sensing layer. Preferably, $CO_2$ may diffuse into the sensing layer and change the pH in said sensing layer by interacting with water, thus increasing the concentration of protons and thus changing the pH.

The term "irradiated with a predetermined radiation" as used herein means that the sensing layer may be irradiated or excited with radiation of a suitable wavelength, in particular a wavelength which is able to generate an optical response of the sensing layer. For example, the irradiation may be carried out with visible light, infrared light and/or ultraviolet light. Preferred examples of a predetermined radiation is light of the green-blue visible spectrum, e.g. of a wavelength of about 400 to 500 nm, e.g. 440 nm, 450 nm, 460 nm, 470 nm, 480 nm, 490 nm etc. The radiation, i.e. the light wavelength as well as its intensity, may in general be made dependent on or be adapted to the optically reactive material in the sensing layer. For specific optically reactive material suitable corresponding excitation wavelengths may be used.

In a preferred embodiment, the sensing layer comprises as optically reactive material a luminescent material. The "luminescent material" may comprise one or more than one dye. The dye may be sensitive for the gas to be measured, e.g. for $CO_2$. The sensitivity may be indirect, for example, be provided via a sensitivity to pH, which in turn is influenced by gas, e.g. $CO_2$, that is diffusing into the sensing layer. Alternatively, the gas may itself have a direct influence on the sensitivity of the dye. In a particularly preferred embodiment, the luminescent material comprises two dyes. For example, the luminescent material may comprise a gas-sensitive dye which works as indicator dye, and a gas-insensitive dye which works as reference dye. In further embodiments, the two dyes as mentioned above may have different decay times. For example, the gas-sensitive dye may have a fast luminescence decay time, whereas the gas-insensitive dye may have a slow luminescence decay time. Examples of suitable reference dyes which are inert to a gas and which show a long decay time include: (1) transition metal complexes with ruthenium(II), rhenium (I), or osmium and iridium as central atom and diimine ligands; (2) phosphorescent porphyrins with platinum, palladium, lutetium or tin as central atom; (3) phosphorescent complexes of rare earths, for instance europium, dysprosium or terbium; and (4) phosphorescent crystals such as ruby, Cr-YAG, alexandrite, or phosphorescent mixed oxides such as magnesium fluoro-germanate. Examples of suitable indicator dyes which are sensitive to a gas and which show a short decay time include 8-Hydroxypyrene-1,3,6-trisulfonic acid, trisodium salt (HPTS), fluorescein, rhodamine B, rhodamine B-octadecyl ester, hexadecyl-acridine orange, hydroxymethyl coumarin, rhodamine, B-octadecyl ester, rhodamine B, naphthofluorescein, sulforhodamine 101, eosin, thionin, and Nile blue. In further specific embodiments, the present invention relates to combinations of reference dyes and indicators dyes, including all combinations of the above indicated exemplified indicators dyes and references dyes. Preferred examples of combinations of reference dyes and indicators dyes to be used in a chemo-optical sensor unit according to the invention include (reference dye/indicator dye): Ruthenium(II)-(tris-4, 7-diphenyl-1, 10-phenantroline)/HPTS; Ruthenium(II)-(tris-4, 7-diphenyl-1,10-phenantroline)/fluorescein; Ruthenium(II)-(tris-4, 7-diphenyl-1,10-phenantroline)/rhodamine B; Ruthenium(II)-(tris-4, 7-diphenyl-1,10-phenantroline)/rhodamine B-octadecyl ester; Ruthenium(II)-(tris-4,7-diphenyl-1,10-phenantroline)/hexadecyl-acridine orange; Europium (III)-tris-theonyl-trifluoromethyl acetonate/ hydroxymethyl coumarin; Platinum (II)-tetraphenylporphyrin/rhodamine B-octadecyl ester; Platinum (II)-tetraphenyl porphyrin/rhodamine B; Platinum (II)-tetraphenyl porphyrin/naphthofluorescein; Platinum (II)-tetraphenyl porphyrin/sulforhodamine 101; Platinum (II)-octaethyl porphyrin/eosin; Platinum (II)-octaethyl porphyrin/thionin; Platinum (II)-octaethyl ketoporphyrin/Nile blue; CR (III)-YAG/Nile blue; and Cr (III)-YAG/naphthofluorescein.

On the basis of a two dye combination in the sensor layer a measurement according to the Dual Lifetime Referencing principle, e.g. as derivable from U.S. Pat. No. 6,602,716 B1 or from Kocincova, New pH Sensitive Sensor Materials; Luminescent Fiber-Optic Dual Sensors for Non-Invasive and Simultaneous Measurement of pH and pO2 (Dissolved Oxygen) in Biological Systems, 2007, PhD thesis, University of Regensburg, may be implemented. In particular, on the basis of the different decay times of the indicator and the reference dye, the intensity of the excitation may be modulated at a fixed frequency and the phase angle of the luminescence signal, which is independent of the amplitudes, may be detected and translated into a relative intensity of the gas-sensitive dye (indicator dye) from which subsequently the gas concentration may be determined.

In specific embodiments the luminescent material may be capable of binding volatile acid molecules and/or volatile base molecules. The sensing layer may comprise luminescent material, which provides this capability, e.g. the luminescent material used as indicator dye.

Accordingly, the sensing layer may be at least transparent for gas molecules such as $O_2$ and/or $CO_2$, which may arrive from a deeper layer such as the gas-permeable layer. Typically, the sensing layer may also be permeable for water molecules, which may diffuse in or out of deeper layers, i.e. layers below the sensing layer according to the osmotic pressure in the corresponding region of the chemo-optical sensor according to the present invention.

In certain specific embodiments, the sensing layer may comprise luminescent material which is capable of measuring the concentration of different gases, or which is capable of measuring the concentration of more than one gas simultaneously, e.g. the concentration of two gases at the same time. For example, the sensing layer may comprise two kinds of luminescent material adapted to the measurement of a different gas, respectively. Preferably, one sub-layer, region or one kind of material may be adapted to detect oxygen and a second sub-layer, region or kind of material is adapted to detect $CO_2$. Further details on multiparameter sensors and additional possibilities of implementing them would be known to the skilled person or can be derive from suitable literature sources such as WO 02/056023 or Schäferling, The Art of Fluorescence Imaging with Chemical Sensors, 2012, Angewandte Chemie International Edition, 51(15), 3532-3554.

The sensing layer may be provided as single layer. In alternative embodiments more than one sensing layer may be provided. Such second or further sensing layer may have the same properties or different properties than the first sensing layer. For example, the second or further sensing layer may comprise different luminescent material, e.g. different dyes, or it may be provided in a different chemical environment such as a different buffer, or having a different pH than a first sensing layer. In further embodiments, a second or subsequent sensing layer may be adapted to measure a different gas, than a first sensing layer, e.g. $O_2$ instead of $CO_2$ which may be measured in a first sensing layer.

The chemo-optical sensor unit may further be adapted to measure an optical response of the at least one sensing layer. Importantly, the received optical response is supposed to depend on the concentration of the gas to be measured. Such an adaption may comprise the provision of suitable detection methods or devices allowing to receive, detect and/or analyze one or more optical responses emanating from the sensing layer. The detection may be performed or implemented according to any suitable detection methods or on the basis of any suitable detection devices or comprising suitable components allowing to perform detection steps or sub-steps.

The term "gas-permeable layer" as used herein refers to a structure which is transparent for gas molecules. Typically, the gas-permeable layer is provided as a membrane structure which is adapted to pass gas to the overlaying sensing layer. In specific embodiments, the gas-permeable layer is transparent for gas molecules such as $O_2$ and/or $CO_2$. Accordingly, the gas-permeable layer may be adapted to pass gas whose concentration is to be measured through the gas-permeable layer towards the sensing layer. The gas whose concentration is to be measured is any gas as defined herein above, preferably $O_2$ and/or $CO_2$, most preferably $CO_2$. Typically, the gas-permeable layer may also be permeable for water molecules in the gas phase, which may diffuse in or out of layers above or below the gas-permeable layer.

The membrane of the gas-permeable layer may be composed of suitable gas and water permeable material. For example, the membrane may be a silicone membrane, or may comprise silicone. Alternatively, the membrane may be composed of or comprise materials such as PTFE (teflon) or derivatives. In further alternative embodiments, the membrane may be composed of or comprise, porous hydrophobic polymers, e.g. based on polypropylene and ethylene or porous hydrophobic silicon oxides such as areogels. Further suitable material would be known to the skilled person and are also envisaged in the context of the present invention.

The gas-permeable layer may further be composed of filler material which is passable for gas molecules. An example of such filler material is silicone rubber material. In a preferred embodiment, the gas-permeable layer may thus comprise silicone rubber or essentially consist of silicon rubber material.

In further preferred embodiments of the present invention, the gas-permeable layer may additionally be adapted to prevent light from passing through the gas-permeable layer. The term "preventing light from passing through the gas-permeable layer" is in particular intended to mean that the gas permeable layer is be adapted to reflect or scatter light transmitted through the at least one sensing layer, and/or to block possible light interferences outside of the intended sensor range. The reflection or scattering of light by the gas permeable layer may be achieved by using any suitable light reflecting material such as metals, e.g. aluminum, or metal oxides. Particularly preferred is the use of titanium compositions, e.g. compositions comprising $TiO_2$. In specific embodiments, the light reflection or scattering may be complete, i.e. for all wavelengths, or it may be specific for certain wavelengths or ranges of wavelengths. For example, light of a certain wavelength or range of wavelengths, in particular of the excitation wavelength for the luminescent material in the sensing layer, may be reflected or scattered, whereas light of a different wavelength which is not excitatory for the luminescent material in the sensing layer may not be reflected. Further, the gas permeable layer may block possible interference of fluorescent molecules, for example outside of the intended detection layer or detection volume, e.g. resulting in a limitation of the optical field view to the intended detection layer. Such a blocking activity may be accomplished by providing light absorbing materials, which work outside of the envisaged sensing range. In specific embodiments, the gas-permeable layer may function as barrier to light and as permeable layer for small molecules such as $CO_2$, $O_2$ or $H_2O$.

The gas-permeable layer may be provided as single layer. In alternative embodiments more than one gas-permeable layer may be provided. Such second or further gas-permeable layer may have the same properties as, or different properties than the first gas-permeable layer. For example, the second or further gas-permeable layer may have the property of reflecting light of a different wavelength. In further embodiments, the second or further gas-permeable layer may have the property of being permeable for different molecules than the first gas-permeable layer. E.g. different gases or different compounds may pass through the first and second or subsequent gas-permeable layer. Typically, gas-permeable layers according to the present invention may have different permeabilities for each passing molecule or for each passing molecule class or category.

In further specific embodiments of the invention the chemo-optical sensor may further comprise at least one optical transparent layer adjacent to the at least one sensing layer. The optical transparent layer may preferably be on top of the sensing layer, which in turn is on top of the gas-permeable layer as defined herein above. The transparent layer may accordingly cover the sensing layer and protect it from direct contact with the surrounding atmosphere, thereby functioning as support layer. Thus, the at least one sensing layer may be enclosed by the gas permeable layer from one side and by the optical transparent layer from the other side. The term "optical transparent layer" as used herein refers to a carrier substrate which is at least partially transparent for radiation. In some embodiments, the optically transparent layer may be transparent for the entire suitable spectrum of electromagnetic waves, e.g. infrared light, visible light and ultraviolet light. In other embodiments, the optically transparent layer may be transparent for specific wavelengths or wavelength ranges only. The optical transparent layer may for example be transparent for the predetermined radiation as described above, or excitation wavelength(s) or wavelengths range(s) for the luminescent material(s) in the sensing layer, whereas light of a different wavelength which is not excitatory for the luminescent material in the sensing layer may not be passed. In addition, the optical transparent layer may be transparent for the light of the optical response generated in the sensing layer. Such light may be provided in a specific wavelength or range of wavelength which may specifically be passed through the optical transparent layer, whereas light of different wavelengths may be passed. In a specific embodiment, the optical transparent layer may only be transparent for excitation wavelength(s) or ranges of wavelength(s) for the luminescent material in the sensing layer and for the wavelength(s) or range of wavelength(s) generated as optical response by said luminescent material in the sensing layer.

The optical transparent layer may be composed of any suitable transparent material known to the skilled person. The optical transparent layer may, for example, be composed of transparent material such as glass, polycarbonate, PET, silicone rubber, or PMMA (Plexiglas).

In further embodiments, the optical transparent layer may be non-permeable for gas, e.g. for $O_2$ and/or $CO_2$.

The chemo-optical sensor unit may further be adapted to operate with a contact medium between the chemo-optical sensor unit and the skin. The term "contact medium" as used herein refers to a medium which may be provided at the interface between the chemo-optical sensor unit and the surface layer on which the measurement of gas is to be carried out, i.e. the skin. Preferably, the contact medium is interposed at least between the lowermost layer of the sensor unit and the surface layer on which the measurement of gas is to be carried out, i.e. the skin of the human or animal body. The contact medium may be a gel or liquid, which typically allows the transfer gas molecules from the deeper layer, e.g. skin, to the chemo-optical sensor unit according to the present invention. Thus, in a particularly preferred embodiment, the contact medium is at least gas-permeable. The gas-permeability may be a general permeability for any gaseous material. Alternatively, the contact medium may have a specific permeability for certain gas molecules, e.g. for $O_2$, $CO_2$, CO, $N_2$, and/or $NH_3$. Particularly preferred is the permeability for $O_2$ and/or $CO_2$. Most preferred is the permeability for $CO_2$. In specific embodiments, the contact medium may be selectively permeable for certain gases and impermeable for other gases. It is preferred that the contact medium be selectively permeable for at least $O_2$ and/or $CO_2$. Most preferred is a selective permeability for $CO_2$.

Furthermore, the contact medium may allow to keep the water content or moisture content of the surface layer on which the measurement of gas is to be carried out, e.g. the skin of the human or animal body stable, or to control the water content or moisture content of the surface layer on which the measurement of gas is to be carried out, e.g. the skin of the human or animal body.

The contact medium is, in further embodiments, characterized as being biocompatible. The term "biocompatible contact medium" as used herein means that the contact medium does not cause a toxic, immunologic, and/or allergic reaction to the surface area of the skin of the human or animal body to which it is applied, or to the body of the person to which it is applied, or any other biologically or medicinal deleterious or harmful reaction, e.g. that it is not carcinogenic.

In certain embodiments, the contact medium may be thermally conductive, e.g. when a heating element or heating device is used. The thermal conductivity may be used to mitigate thermal changes of the chemo-optical sensor unit, i.e. to minimize a temperature difference between the chemo-optical sensor and the skin area underlying the contact medium. Thereby a constant temperature at the chemo-optical sensor unit can be achieved, thus allowing for an accurate measurement of the concentration of a gas. A contact medium which is not thermally conductive may, for example, be employed if the induction of vasodilatation is envisaged, e.g. by using a chemical compound such as capsicum.

In a central aspect the present invention provides a chemo-optical sensor unit as defined herein which comprises at least one volatile acid and/or base binding layer. The volatile acid and/or base binding layer is typically located in the gas-pathway from the skin to the sensing layer as defined above. Furthermore, the volatile acid and/or base binding layer is adapted to pass gas whose concentration is to be measured through the volatile acid and/or base binding layer.

The term "volatile acid" as used herein refers to a molecule which becomes an acid, i.e. dissociates an H', when in contact with water and which is capable of becoming volatile, i.e. air based, at the interface of the chemo-optical sensor, e.g. on the skin of a human being or animal, or in the environment of the chemo-optical sensor, e.g. during storage of the sensor etc. Typically, the volatile acid according to the present invention is a stronger acid than carbonic acid ($H_2CO_3$). Examples of volatile acids include HCl, acetic acid, $H_2SO_3$, lactic acid, formic acid, butyric acid, hydrogen sulphide ($H_2S$) and propionic acid. The volatile acids may be present in an essentially physiological range of concentrations, but may also extend this range of concentrations, e.g. due to influences by a subject's health conditions, a subject's medication or food intake, e.g. the consumption of garlic, onions, red pepper etc. The range may further depend on the climate, the air pressure, or the typical temperature in the patient's surrounding or other factors which are known to change the volatility of a molecule. The volatile acid's concentration may, in specific embodiments, also have non-physiological values, e.g. in cases in which the chemo-optical sensor is stored or shelved in volatile acid containing environments, e.g. in air polluted environments or environments comprising smoke, e.g. cigarette smoke, industrial smoke or dust.

The term "volatile base" as used herein refers to a molecule which becomes a base, i.e. dissociates an $OH^-$, when in contact with water and which is capable of becoming volatile, i.e. air based, at the interface of the chemo-optical sensor, e.g. on the skin of a human being or animal, or in the environment of the chemo-optical sensor, e.g. during storage of the sensor etc. Examples of volatile bases include ammonia, methylamine, ethylamine, diethylamine, triethylamine, isobutylamine, piperazine, or ethylenediamine. The volatile bases may be present in an essentially physiological range of concentrations, but may also extend this range of concentrations, e.g. due to influences by a subject's health conditions, for instance due to kidney diseases or diabetes, a subject's medication or food intake etc., or as result of a subject's sweating. The range may further depend on the climate, the air pressure, or the typical temperature in the patient's surrounding or other factors which are known to change the volatility of a molecule. The volatile base's concentration may, in specific embodiments, also have non-physiological values, e.g. in cases in which the chemo-optical sensor is stored or shelved in volatile bases containing environments, e.g. in air polluted environments.

A "volatile acid and/or base binding layer" as mentioned throughout the description refers to a structure within the chemo-optical sensor unit which is capable of binding a volatile acid and/or a volatile base as defined above. This structure typically comprises one or more compounds, which are capable of binding to one or more volatile base(s), or which comprise compounds, e.g. different compounds, which are, e.g. in combination, capable of binding to one or more volatile acid(s) and to one or more volatile base(s). The binding process may comprise a physical or chemical linkage of the volatile acid or volatile base to compounds or structural elements present in the binding layer, thus achieving an immobilization of the volatile acid(s) and/or volatile base(s), a chemical or biochemical conversion of the volatile acid(s) and/or volatile base(s) into non-volatile derivatives, and/or a transient retention or storage of the volatile acids and/or volatile bases. In specific embodiments, the volatile acid and/or base binding layer, i.e. a compound within this layer, may further be capable of converting said volatile acid(s) into less acidic volatile molecules, or be capable of converting said volatile base(s) into less alkaline volatile molecules. In certain embodiments, the present invention also envisages a combination of two or more of the mentioned principles or binding possibilities in one layer or in one chemo-optical sensor unit.

The binding of volatile acid(s) and/or volatile base(s) via a chemical linkage of the volatile acids or volatile bases may, for example, be implemented by a compound having or comprising a chemical structure or moiety which is capable of reacting with the volatile acid or the volatile base and thereby produces a covalent binding or strong non-covalent binding between the volatile acid or base and the chemical structure, e.g. a binding based on ionic forces, or van-der Waals forces.

The binding of volatile acid(s) and/or volatile base(s) via a physical linkage of the volatile acids or volatile bases may be implemented by a compound having or comprising a physical structure which is capable of absorbing the volatile acid or volatile base and thereby provides an intimate contact between said structure and the volatile acid or volatile base which does not allow the volatile acid or volatile base to leave the structure, preferably within physiological concentrations of the volatile acid or volatile base or concentrations typical for shelving and storing the chemo-optical sensor. This intimate contact may preferably be a permanent contact, at least under physiological or typical use conditions. Such physical structures may be, for example, a porous matrix or a mesh structure, or a structure comprising cavities or a lattice texture, e.g. in ion exchange resins.

The binding of the volatile acid(s) and/or volatile base(s) via a chemical or biochemical conversion of the volatile acids or volatile bases into non-volatile derivatives may, for example, be implemented by providing a compound representing one or more reaction partners for volatile acids, or a compound representing one or more reaction partners for volatile bases, which chemically or biochemically transform the volatile acid(s) or the volatile base(s). Chemical reaction partners may be, for example, organic or inorganic bases. The result(s) of such conversion reactions may, for example, be the addition of chemical moieties to the volatile acid or volatile base molecule, thus reducing its volatility, or preferably immobilizing the molecule in the binding layer. Biochemical transformation reactions may be performed, for example, by enzymes which are capable of binding to the volatile acid(s) and/or volatile base(s) and of chemically modifying the volatile acid(s) and/or volatile base(s). The binding may be a specific binding. The result of such biochemical conversion may be the addition of chemical/biochemical entities, e.g. chemical moieties, to the volatile acid molecule or the volatile base molecule, thus reducing its volatility, preferably immobilizing the molecule in the binding layer. The enzymes may be provided in a long-lasting conformation, e.g. in a suitable buffer and kept at suitable temperatures.

The alternatively provided possibility of converting the volatile acid(s) into less acidic volatile molecules, which is also envisaged by the present invention, means that the volatile acid is not immobilized in the binding layer, but converted into a still volatile, but less acidic molecule. Such molecule may be capable of passing through the binding layer towards the gas-permeable layer and/or the sensing layer. Due to its reduced acidity, there is a reduced or no impact on the functionality of the sensing layer. In a preferred embodiment, the acidity may be reduced such that the resulting volatile acid is not stronger than carbonic acid, i.e. that its pKa is not lower and/or its pH is not lower than that of carbonic acid.

The further provided possibility of converting the volatile base(s) into less alkaline volatile molecules, which is envisaged by the present invention, means that the volatile base is not immobilized in the binding layer, but converted into a still volatile, but less alkaline molecule. Such molecule may be capable of passing through the binding layer towards the gas-permeable layer and/or the sensing layer. Due to its reduced alkalinity, there is a reduced or no impact on the functionality of the sensing layer.

The binding of the volatile acid(s) and/or volatile base(s) via a transient retention or storage of the volatile acids and/or bases may be conveyed by compounds with buffering capabilities. Such transient retention compounds may be physical elements which allow to adsorb the volatile acid(s) and/or base(s), e.g. structures having 3 dimensional shapes with high binding capacity or chemical functions of high adsorbility, and which also allow to set the adsorbed molecules free, e.g. if a certain partial pressure threshold is surpassed, or if a secondary parameter such as temperature or pH is changed. The transient retention compounds may alternatively also be chemical entities, which are able to adsorb the acids or bases transiently, e.g. via transient or weak binding forces, and which, upon the change of secondary parameters such as temperature, or pH release said volatile acid(s) or said volatile base(s).

In particularly preferred embodiments of the invention the compound capable of binding or converting a volatile acid or a volatile base is a chemical buffer. The term "chemical buffer" as used herein refers to an aqueous solution or gel-like composition typically comprising a mixture of a weak acid and its conjugate base or a weak base and its conjugate acid. Examples of chemical buffers which may be used in the context of the present invention are citric acid based buffers, acetic acid based buffers, phosphate based buffers, N-Cyclohexyl-2-aminoethanesulfonic acid (CHES) based buffers, and borate based buffers. Also envisaged are chemical buffers such as 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic Acid (TAPSO), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES) and 2(R)-2-(methylamino)succinic acid (succinic acid).

In a preferred embodiment, the compound capable of immobilizing or converting volatile acid(s) and/or base(s) is biocompatible. The term "biocompatible compound capable of immobilizing or converting volatile acid(s) and/or base(s)" as used herein means that the compound does not cause a toxic, immunologic, and/or allergic reaction to the surface area of the skin of the human or animal body to which it is applied, or to the body of the person to which it is applied, or any other biologically or medicinal deleterious or harmful reaction, e.g. that it is not carcinogenic. These properties include also a lack of moveability towards the skin in case the compound is not in direct contact with the skin. Such lack of moveability of the compound may result in biocompatibility even in cases in which the compound is known or suspected to be toxic or problematic etc. In specific embodiments, toxic, immunologic or allergic reactions caused by ingredients of the volatile acid and/or base binding layer may be mitigated or blocked by the presence of counter activities, e.g. the blocking agents, antidotes etc.

Particularly preferred are biocompatible chemical buffers of the group of phosphate buffers. Examples of suitable phosphate buffers are $K_2HPO_4$ buffers and $Na_2HPO_4$ buffers.

In certain embodiments of the invention the at least one volatile acid and/or base binding layer may be capable of attracting and binding 70%, 80%, 90%, 95%, 96%, 97%, 98%, 99% or more of the volatile acids and/or bases entering the chemo-optical sensor unit. The capacity of the binding layer to attract and bind volatile acids and/or volatile bases may particularly be influenced by the exposure time to a volatile acid or volatile base. Thus, the longer the exposure time, e.g. on the skin or during the storage of the chemo-optical sensor before its use, e.g. in dusty or smoke contaminated environments, the higher the amount of volatile acids or bases which can enter the chemo-optical sensor. In order to adapt the binding capacity of a binding layer as defined herein to different potential exposure times of volatile acids and/or volatile bases, the amount or concentration of compounds capable of immobilizing or converting volatile acid(s) and/or base(s) in the binding layer may be adjusted accordingly. For example, if a certain shelf life of the chemo-optical sensor layer is foreseeable, or if it is foreseeable that the packaged chemo-optical sensor might be exposed to smoke or dust contaminated environments, the amount or concentration of compounds capable of immobilizing or converting volatile acid(s) and/or base(s) in the binding layer may be increased such that it is possible to bind the maximum expected amount of volatile acids and/or bases during the entire life cycle of the chemo-optical sensor, i.e. including its typical use on the skin. If, in other embodiments, the chemo-optical sensor is known to be used in the context of surveillance of patients which are affected by a disease or medical condition that leads to an increase of volatile acids on the skin, the amount or concentration of compounds capable of immobilizing or converting volatile acid(s) and/or base(s) in the binding layer may be adapted to this specific situation. For instance, the amount or concentration of the binding compounds may be increased. Suitable amounts or concentrations as mentioned herein may be known to the skilled person or can be determined on the basis of reference measurements, or derived from suitable test procedures. It is accordingly preferred that the at least one volatile acid and/or base binding layer may be capable of attracting and binding 70%, 80%, 90%, 95%, 96%, 97%, 98%, 99% or more of the volatile acids and/or bases entering the chemo-optical sensor unit during the period of transcutaneous measurement and/or during the period of storage of the chemo-optical sensor before usage.

The amount of attracted and/or bound molecules may depend on the binding principle or the identity of the binding compound as defined herein above, or on the concrete physiological situation of a patient. In particular, in case, a very high or unusually high amount of volatile acid(s) and/or base(s) is entering the chemo-optical sensor, a lower amount of the volatile acids and/or bases may be attracted and/or bound. It is, however, envisaged by the present invention to avoid such situations by adjusting the binding capacity of the binding layer to the assumed or expected amount of volatile acids or bases present.

It is preferred that between about 80% and 99%, more preferably more than 99%, or even 100% of the volatile acids and/or bases are attracted and/or bound by the volatile acid and/or base binding layer. It is particularly preferred that between about 80% and 99%, more preferably more than 99%, or even 100% of the volatile acids and/or bases are attracted and/or bound by the volatile acid and/or base binding layer during the period of transcutaneous measurement and/or during the period of storage of the chemo-optical sensor before usage. For example 80%, 85%, 90%, 95%, 96%, 97%, 98% or 99%, 99.9%, 99.99%, or 100% of the volatile acids and/or bases entering the chemo-optical sensor unit may be are attracted and/or bound by the volatile acid and/or base binding layer. Specifically, 80%, 85%, 90%, 95%, 96%, 97%, 98% or 99%, 99.9%, 99.99%, or 100% of the volatile acids and/or bases entering the chemo-optical sensor unit may be are attracted and/or bound by the volatile acid and/or base binding layer are attracted and/or bound by the volatile acid and/or base binding layer during the period of transcutaneous measurement and/or during the period of storage of the chemo-optical sensor before usage. The period of transcutaneous measurement may be any suitable period of time, for example, a period of about 5 min to 24 h, preferably a period of about 1 to 15 h, e.g. 1 h, 2 h, 3 h, 4 h, 5 h, 6 h, 7 h, 8 h, 9 h, 10 h, 11 h, 12 h, 13 h, 14 h, 15 h or any value in between these values. The period of storage of the chemo-optical sensor before usage may be any suitable period of time during which the chemo-optical sensor may be stored such that it can be used, i.e. it refers to a shelf life of the chemo-optical sensor. The period of storage of the chemo-optical sensor may, for example, be a period up to 6 months, 7 months, 8 months, 9 months, 10 months, 11 months, 1 year, or more than one year, e.g. 18 months or 24 months or any value in between these values.

In a further specific embodiment of the present invention the capacity of the binding layer to attract and bind volatile acids and/or volatile bases may be such that during usage, i.e. during the period of transcutaneous measurement and/or the period of storage of the chemo-optical sensor before usage, e.g. as defined above, only a minimal non-reversible $CO_2$ sensitivity change may occur. Preferably, during a storage period of about 1 year of the chemo-optical sensor a non-reversible $CO_2$ sensitivity change of about 10%, more preferably of about 8% 7%, 6%, 5%, 4%, 3%, 2%, or most preferably of about 1% or less than 1% may occur. In a different embodiment, during a typical usage of the chemo-optical sensor in transcutaneous measurement of about 8 to 10 hours a non-reversible $CO_2$ sensitivity change of about 10%, more preferably of about 8% 7%, 6%, 5%, 4%, 3%, 2%, or most preferably of about 1% or less than 1% may occur. In another embodiment, during a storage period of about 1 year of the chemo-optical sensor and during a subsequent usage of the chemo-optical sensor in transcutaneous measurement of about 8 to 10 hours a non-reversible $CO_2$ sensitivity change of about 10%, more preferably of about 8% 7%, 6%, 5%, 4%, 3%, 2%, or most preferably of about 1% or less than 1% may occur.

In very specific embodiments of the present invention said volatile acid and/or base binding layer may comprise luminescent material, preferably luminescent material as defined herein above. Preferably, the volatile acid and/or base binding layer may comprise transition metal complexes with ruthenium(II), rhenium (I), or osmium and iridium as central atom and diimine ligands; (2) phosphorescent porphyrins with platinum, palladium, lutetium or tin as central atom; (3) phosphorescent complexes of rare earths, for instance europium, dysprosium or terbium; and (4) phosphorescent crystals such as ruby, Cr-YAG, alexandrite, or phosphorescent mixed oxides such as magnesium fluoro-germanate, 8-Hydroxypyrene-1,3,6-trisulfonic acid, trisodium salt (HPTS), fluorescein, rhodamine B, rhodamine B-octadecyl ester, hexadecyl-acridine orange, hydroxymethyl coumarin, rhodamine, B-octadecyl ester, rhodamine B, naphthofluorescein, sulforhodamine 101, eosin, thionin, Nile blue or combinations dyes such as Ruthenium(II)-(tris-4, 7-diphenyl-1, 10-phenantroline)/HPTS; Ruthenium(II)-(tris-4, 7-diphenyl-1,10-phenantroline)/fluorescein; Ruthenium(II)-(tris-4, 7-diphenyl-1,10-phenantroline)/rhodamine B; Ruthenium (II)-(tris-4, 7-diphenyl-1,10-phenantroline)/rhodamine B-octadecyl ester; Ruthenium(II)-(tris-4,7-diphenyl-1,10-phenantroline)/hexadecyl-acridine orange; Europium (III)-tris-theonyl-trifluoromethyl acetonate/hydroxymethyl coumarin; Platinum (II)-tetraphenylporphyrin/rhodamine B-octadecyl ester; Platinum (II)-tetraphenyl porphyrin/rhodamine B; Platinum (II)-tetraphenyl porphyrin/naphthofluorescein; Platinum (II)-tetraphenyl porphyrin/sulforhodamine 101; Platinum (II)-octaethyl porphyrin/eosin; Platinum (II)-octaethyl porphyrin/thionin; Platinum (II)-octaethyl ketoporphyrin/Nile blue; CR (III)-YAG/Nile blue; and Cr (III)-YAG/naphthofluorescein. Such luminescent material, e.g. a dye or combination of dyes as mentioned above, may be capable of binding volatile acids and/or bases, e.g. by adsorption.

The volatile acid and/or base binding layer may comprise the compounds capable of immobilizing or converting volatile acid(s) and/or base(s) in any suitable concentration or amount. The concentration should preferably be chosen such that the typical amount of volatile acids or the typical amount of volatile bases, e.g. within physiological ranges, or within an extended physiological range which also covers extreme situations such as diseases leading to increased production of volatile acids or volatile bases, medication or food intake, e.g. the consumption of garlic, onions, red pepper etc. leading to increased production of volatile acids or bases; or climatic or temperature extremes during the use of the chemo-optical sensor. The concentration or amount to be used may depend on the compound to be employed and may be adjusted by the skilled person according to data of the general knowledge with respect to said compound.

The volatile acid and/or base binding layer may further comprise the compounds capable of immobilizing or converting volatile acid(s) and/or base(s) in any suitable molecular environment or physico-chemical context. For example, the binding layer may be composed of filler material which is passable for gas molecules, in particular $O_2$ and/or $CO_2$. A preferred example of such filler material is silicone rubber material. In a preferred embodiment, the binding layer may thus comprise silicone rubber or essentially consist of silicone rubber material. The binding layer may further comprise compounds such as water or additional molecules. The binding layer may additionally or alternatively comprise structural elements which support physical elements as mentioned herein above, e.g. matrices, meshes, adsorption elements etc. The binding layer may further comprise stabilizing or buffering systems for catalytic enzymes which allow to convert the volatile acid(s) and/or base(s).

In further specific embodiments, the volatile acid and/or base binding layer may have any suitable thickness. For example, the volatile acid and/or base binding layer may have a thickness of about 10% to about 300% of the thickness of the at least one sensing layer or the at least one gas-permeable layer as defined herein above. The binding layer may thus, in one embodiment, have a thickness of about 10%, 20%, 30%, 40%, 50%, 60%, 70%, 80%, 90%, 100%, 110%, 120%, 130% 140%, 150%, 160%, 170%, 180%, 190%, 200%, 210%, 220%, 230%, 240%, 250%, 260%, 270%, 280%, 290% or 300% or more of the thickness of the at least one sensing layer as define herein above, or any value in between the indicated values. In a further embodiment, the binding layer may have a thickness of about 10%, 20%, 30%, 40%, 50%, 60%, 70%, 80%, 90%, 100%, 110%, 120%, 130% 140%, 150%, 160%, 170%, 180%, 190%, 200%, 210%, 220%, 230%, 240%, 250%, 260%, 270%, 280%, 290% or 300% or more of the thickness of the at least at least one gas-permeable layer as defined herein above, or any value in between the indicated values.

In a particularly preferred embodiment of the present invention, the volatile acid and/or base binding layer may have the same or a very similar composition as the sensing layer as defined herein above. For example, the volatile acid and/or base binding layer and the sensing layer may comprise the same dye molecules or the same combination of dye molecules. Additionally, both layers may be comprises of the same structural elements or fillers, e.g. comprise silicon rubber. The concentration of the dye molecules may be identical or be different in both layers. E.g. in the volatile acid and/or base binding layer(s) the concentration of the dye molecules may be increased, e.g. by 10%, 20%, 30%, 40%, 50%, 60%, 70%, 80%, 90%, 100% or more in comparison to the sensing layer(s).

In further specific embodiments, the thickness of the volatile acid and/or base binding layer may be the same or very similar in comparison to the sensing layer. For example, the thickness of the volatile acid and/or base binding layer may be 80%, 90%, 100%, 110%, or 120% or any value on between these values of the thickness of the sensing layer.

The volatile acid and/or base binding layer may further be provided in any suitable form or shape. The layer may, for example, be a continuous layer or a non-continuous layer. As a non-continuous layer, it may be comprised of a sequence of blocks of volatile acid and/or base binding layer and gaps between these blocks. The blocks may have the features of the layer as defined herein above, e.g. the thickness etc. as defined herein above. There may be a single sequence of a block, a gap and a further block. In alternative embodiments, the volatile acid and/or base binding layer may be provided as a multiple sequence of several blocks and interspersed gaps. The blocks and/or gaps may have identical lengths or sizes, or may differ in length and size. In case there are gaps between blocks of volatile acid and/or base binding layer, subjacent layers may fill the gap. In preferred embodiments, the volatile acid and/or base binding layer may be connected via a contact medium with the deeper layer, i.e. with the skin of the animal or human body. Accordingly, contact medium as defined herein above may fill in the one or multiple gaps as mentioned above. It is thus preferred that the contact medium is allowed to directly contact the next higher level or layer of the chemo-optical sensor, e.g. the at least one gas-permeable layer as defined herein above.

In a further specific embodiment the present invention provides a chemo-optical sensor unit as defined herein which is provided in a conditioning fluid. The provision may be, for example, a packaging, storing, keeping, suspending of the chemo-optical sensor in the conditioning fluid. This may be a short term activity, e.g. of 10 to 60 minutes, or 1 to 24 h, or a longer term activity of 1 day to several months or years, e.g. 2 months, 3 months, 4 months, 5 months, 6 months, 12 months, 24 months or more or any time period in between the indicated values. The term "conditioning fluid" as used herein refers to a liquid or gel-like substance, which keeps the chemo-optical sensor unit in state which allows its immediate use or application without previous calibration or preparation steps. The conditioning fluid may, for example, allow to keep the water content or moisture content of the surface layer on which the measurement of gas is to be carried out stable. The conditioning fluid may further be biocompatible, i.e. it may be non-toxic, non-immunogenic, and/or non-allergenic. In specific embodiments, toxic, immunologic or allergic reactions caused by ingredients of the conditioning fluid may be mitigated or blocked by the presence of counter activities, e.g. the blocking agents, antidotes etc.

In a specific embodiment of the present invention, the conditioning fluid is similar to the contact medium, e.g. comprising most of the components of the contact medium. In further preferred embodiments, the conditioning fluid is essentially identical to the contact medium as defined herein, or is identical to the contact medium as defined herein. Accordingly, a chemo-optical sensor as defined herein may be stored, kept, packaged etc. in contact medium as defined herein above or below.

In further embodiments of the present invention, the chemo-optical device comprises a gas-permeable sensing layer, a first gas-permeable layer, a volatile acid and/or base binding layer and additionally at least a further, second gas-permeable layer. This second gas-permeable layer may be adjacent to one side of the at least one volatile acid and/or base binding layer or to one side of the first gas-permeable layer. The second gas-permeable layer functions as the first gas-permeable layer and is thus adapted to pass gas whose concentration is to be measured towards the sensing layer. In certain embodiments, the second gas-permeable layer may be identical or very similar to the first gas-permeable layer, e.g. have the same or essentially the same composition, have the same or essentially the same thickness etc.

In a particularly preferred embodiment, the mentioned second gas-permeable layer may further be adapted to prevent ions to pass from the chemo-optical sensor unit to the skin, or from the skin into the chemo-optical sensor unit. Thus, the second gas-permeable layer may have an additional function in stopping or reducing ionic movement to and from the sensing layer or the skin.

In a further specific embodiment a chemo-optical sensor unit comprising at least a gas-permeable sensing layer as defined herein above and a gas-permeable layer adjacent to the sensing layer as defined herein above, or any other form or embodiment of the chemo-optical sensor unit as described herein above, may be operated with a contact medium as defined above which is adapted to prevent ions to pass from the chemo-optical sensor unit to the skin, or from the skin into the chemo-optical sensor unit. Thus, the contact medium may have an additional function in stopping or reducing ionic movement to and from the sensing layer or the skin.

The present invention also envisages a chemo-optical sensor unit comprising at least a gas-permeable sensing layer as defined herein above and a gas-permeable layer adjacent to the sensing layer as defined herein above, or any other form or embodiment of the chemo-optical sensor unit as described herein above, which additionally comprises a contact medium as defined above which is adapted to prevent ions to pass from the chemo-optical sensor unit to the skin, or from the skin into the chemo-optical sensor unit. Thus, the contact medium comprised in the chemo-optical sensor unit may have an additional function in stopping or reducing ionic movement, e.g. of ions as defined herein, especially of ions which are associated with volatile acids or volatile bases, to and from the sensing layer of the skin.

One embodiment of the present invention relates to a chemo-optical sensor unit comprising at least one gas-permeable sensing layer as defined herein above and at least one gas-permeable layer adjacent to the sensing layer as defined herein above, at least one volatile acid and/or base binding layer in the gas-pathway from the skin to the sensing layer, or any other form or embodiment of the chemo-optical sensor unit as described herein above, wherein the chemo-optical sensor additionally comprises a contact medium as defined above, which comprises an ion-balancing means capable of removing ions (3) associated with volatile acids and/or bases (11).

A further aspect of the invention relates to the use of a chemo-optical sensor for measurement of a concentration of a gas comprising:

A chemo-optical sensor unit for transcutaneous measurement of a concentration of a gas, comprising:
- at least one gas-permeable sensing layer (2) adapted to be irradiated with a predetermined radiation (5); and
- at least a first gas-permeable layer (3) adjacent to one side of the at least one sensing layer (2), adapted to pass gas whose concentration is to be measured (6) through the gas-permeable layer (3) towards the sensing layer (2);
- at least one volatile acid and/or base binding layer (20) in the gas-pathway from the skin (10) to the sensing layer (2); adapted to pass gas whose concentration is to be measured (6) through the volatile acid and/or base binding layer (20) towards the sensing layer (2);

wherein said chemo-optical sensor unit is adapted to operate with a contact medium (12) between the chemo-optical sensor unit and the skin (10) and wherein the chemo-optical sensor unit is adapted to measure an optical response of the at least one sensing layer (2), whose optical response depends on the concentration of the gas (6), wherein the contact medium (12) comprises an ion-blancing means capale of removing the ions (30) associated with volatile acids and/or bases.

Alternatively, the present invention envisages a chemo-optical sensor unit comprising at least a gas-permeable sensing layer as defined herein above and a gas-permeable layer adjacent to the sensing layer as defined herein above, or any other form or embodiment of the chemo-optical sensor unit as described herein above, which comprises a conditioning fluid as defined above which is adapted to prevent ions to pass from the chemo-optical sensor unit to the skin, or from the skin into the chemo-optical sensor unit, preferably a conditioning fluid which is essentially identical or identical to the contact medium as define herein above. Thus, the conditioning fluid comprised in the chemo-optical sensor unit may have an additional function in stopping or reducing ionic movement to and from the sensing layer of the skin.

The term "ion" as used in this context means a non-volatile ionic entity, preferably a non-volatile ionic entity in an aqueous solution. Such ionic entities may be ions which are associated with volatile acids or bases, e.g. dissociation products from volatile acids or acid forming molecules, including salts (e.g. NaCl), or dissociation products from volatile bases or bases forming molecules. The term also refers to ionic entities which are not associated with volatile acids or volatile bases and are primarily present in a layer of the chemo-optical sensor, e.g. in the gas-permeable layer, the sensing layer and/or the volatile acid and/or base binding layer. Such ionic entities may, for example, be derived from, be associated with or be compounds capable of binding a volatile acid or a volatile base as defined herein above. Typically, such ions may be components of chemical buffers as mentioned herein above. Examples of ions which can move in or out of the chemo-optical sensor and which can be stopped by a second gas-permeable layer or a contact medium or conditioning fluid typically include all ions except those which are associated with $CO_2$. The term "ionic movement to the sensing layer" or "passing of ions from the skin to the chemo-optical sensor unit" as used herein refers to the movement of ionic entities such as ions which are associated with volatile acids or volatile bases, e.g. ions as defined herein above, which may enter the chemo-optical sensor unit from the skin.

The term "ionic movement to the skin" or "passing of ions from the chemo-optical sensor unit to the skin" as used herein refers to the movement of ionic entities such as ionic entities which are not associated with volatile acids or volatile bases and are primarily present in a layer of the chemo-optical sensor, e.g. ions as defined herein above, which may enter the enter the skin from the chemo-optical sensor unit.

The function of stopping or reducing ionic movement to and from the chemo-optical sensor unit may be accomplished by an ion-balancing means. The term "ion balancing means" as used herein refers to a means which is capable of trapping, absorbing and/or exchanging ions, thus leading to a removal or exchange of ions from the ion balancing mean's environment. There are several examples of suitable ion balancing means which would be known to the skilled person. Within the context of the present invention, a preferred ion balancing means may be an ion-trapping means, an ion-exchange polymer, an ion-exchange resin. The ion balancing means may, thus, for example be an ion-exchange polymer or an ion-exchange resin, which absorbs ions from a solution and replaces them by other ions. The present invention further envisages the employment of more than one type of ion balancing means within the context of a chemo-optical sensor unit. For example two, three, four or more different ion balancing means may be used, e.g. within one layer, or within the contact medium. These different ion-balancing means may be based on identical, similar or different principle of ion removal or exchange. In specific embodiments, there may be two types of ion balancing means, one adapted to the stopping of ions associated with volatile acids or volatile bases as defined herein, e.g. coming from the skin, and a second adapted to the stopping of ions coming from the chemo-optical sensor unit and passing on to the skin. Such different selectivities may be implemented by using materials which are able to selectively absorb or bind ions of one or the other type.

Particularly preferred is the presence of an anion-exchange resin in the second gas-permeable layer as defined herein above. Suitable examples of anion-exchange resins would be known to the skilled person or can be derived from suitable literature sources. The anion exchange resin may accordingly bind ionic forms of the volatile acids or volatile bases or associated with the volatile acids or volatile bases and exchange them by non-volatile ions.

It is of note in this context, that $CO_2$ may also be present in ionic form in any of the layers of the chemo-optical sensor according to the present invention, typically as $HCO_3^-$, e.g. when dissolved in water. The presence of an ion-balancing means may thus have an influence on the amount of $CO_2$ molecules which reach the sensing layer. The present invention therefore envisages that an ion balancing means to be used is configured to have a low binding affinity for $HCO_3^-$ and thereby may reach a state of saturation with respect to these ions in a short period of time. Upon saturation of the ion-balancing means there will be no influence on the $CO_2$ concentration. In a preferred embodiment, the ion-balancing means may, upon saturation for $HCO_3^-$ still bind other ions, e.g. ions associated with volatile acids or volatile bases as defined herein above.

In a specific embodiment the present invention thus relates to a chemo-optical sensor unit comprising an ion-balancing means in a saturated state with respect to ions derived from the $CO_2$ molecule, e.g. when dissolved in water, or an ion-balancing means being in a conformation allowing a rapid saturation, e.g. within seconds to several minutes, such as 10 sec to 5 min with ions derived from the $CO_2$ molecule, e.g. when dissolved in water.

FIG. 1 shows schematically a chemo-optical sensor unit comprising a support layer 1, a sensing layer 2 and a gas-permeable layer 3. The sensor unit is adapted to be irradiated with a predetermined radiation 5. Further, an optical response 4 of the sensing layer 2 is shown. The chemo-optical sensor unit is capable of measuring the concentration of gas 6 which enters the unit. The size or thickness 7 of the sensor unit may be varied. In certain embodiments it will be in the range of about 0.2 to about 0.6 mm. In specific embodiments the chemo-optical sensor may comprise a support layer with an optical transparent carrier, a sensing layer, which may comprise a silicone membrane, a reference dye and an indicator dye, which is transparent to gas and pH sensitive, as well as a layer which is transparent to gas and reflective to light, which may, for example, comprise $TiO_2$ in a silicone membrane. The chemo-optical sensor may in further embodiments, for example, be excited at 470 nm (blue-green LED) (5) and the luminescence (4) may, for example, be detected from indicator and reference dyes in the range of 500 to 700 nm (red). The reference dye may preferably have a slow response and the luminophores may be packed in spheres to protect them from $O_2$. The indicator dye may, for example, have a fast response and it may be primary sensitive to H' (pH), leading to an decrease of the amplitude and a yellow coloring under white light illumination due to pH decrease caused by $CO_2$ increase. The frequency of the illumination light intensity modulation may in specific embodiments be chosen such that a phase shift at about 45° can be obtained at low (environmental) $CO_2$ concentrations (6).

Figure 2:
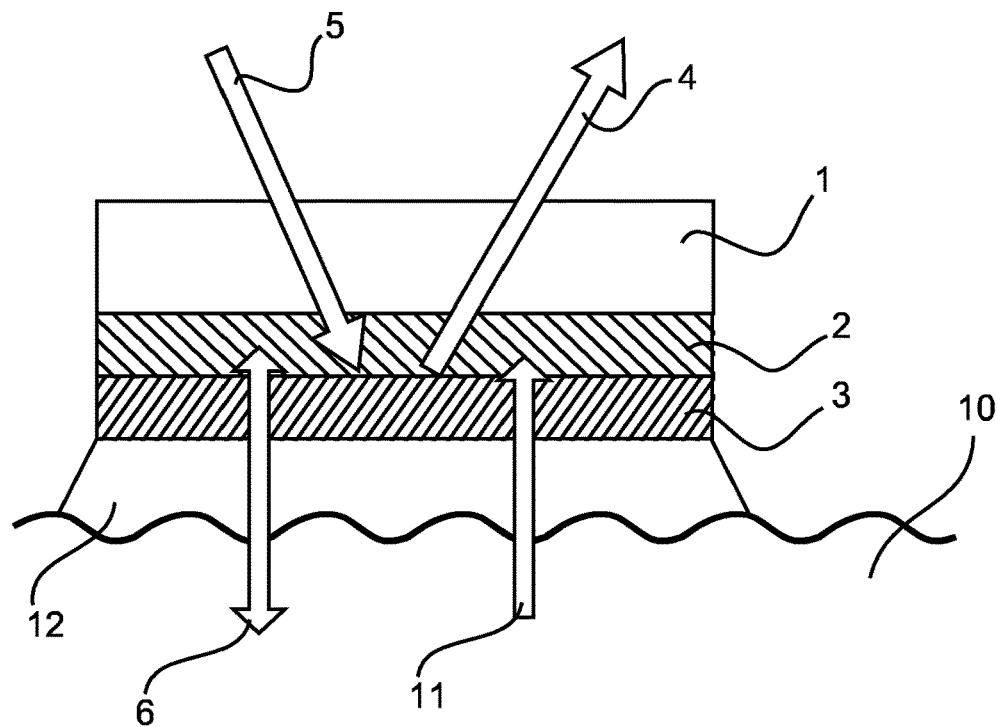
FIG. 2 shows the same principle as outlined in FIG. 1 including the intrusion of volatile acids into the chemo-optical sensor from the epidermis or deeper skin tissue.

FIG. 2 shows a specific employment of the chemo-optical sensor unit, which is operated with a contact medium 12 between the chemo-optical sensor unit and the skin 10, in particular the epidermis of the skin. The FIG. shows the entry of volatile acids and/or volatile bases 11 into the sensor via the gas permeable layer 3 and into to the sensing layer 2.

Figure 3:
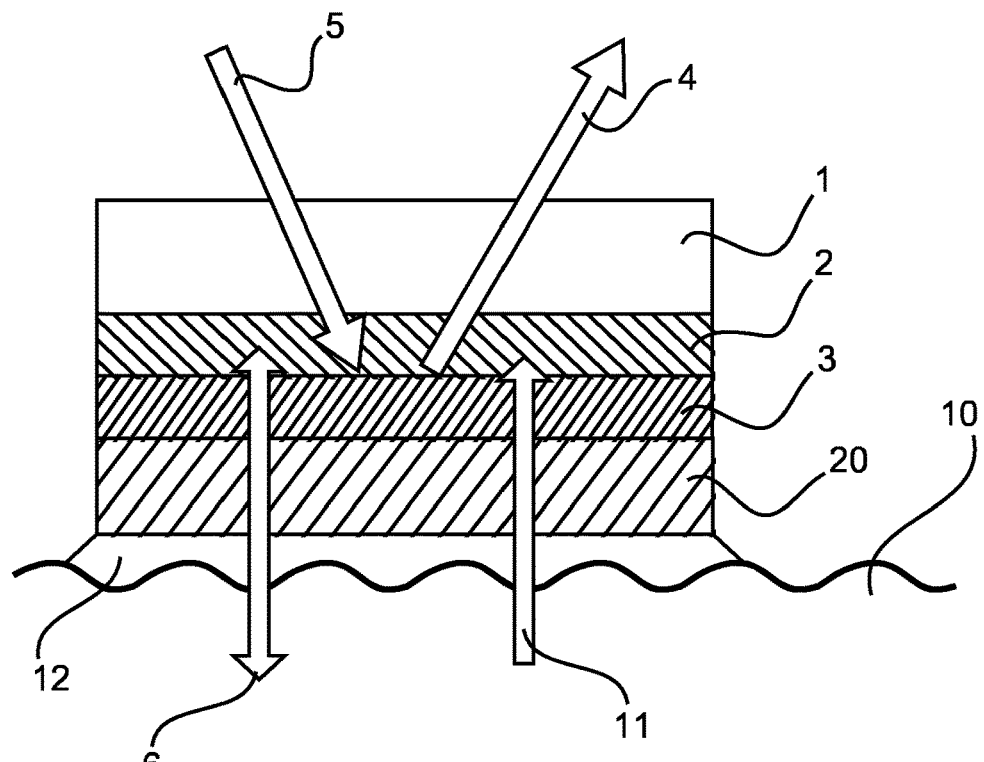
FIG. 3 shows the same composition as FIG. 2 which further includes a volatile acid and/or base binding layer.

In FIG. 3 an embodiment of the chemo-optical sensor according to the present invention is shown. The chemo-optical sensor comprises a support layer 1 as defined herein, a sensing layer 2 as defined herein, one gas-permeable layer adjacent to the sensing layer 3 as defined herein and a volatile acid and/or base binding layer 20 as defined herein. It is further operated with a contact medium 12 between the sensor unit and the skin 10. The contact medium 12 may comprise ion-balancing means as defined herein. The present invention further envisages variants of this embodiment, which comprise more than one volatile acid and/or base binding layer 20, e.g. a second volatile acid and/or base binding layer 20 between the sensing layer 2 and the gas-permeable layer 3, or which comprise the volatile acid and/or base binding layer 20 in a different thickness with respect to the sensing layer 2 or the gas-permeable layer 3. Volatile acids and/or volatile bases 11 may enter the chemo-optical sensor unit via the contact medium 12 and be bound or converted in volatile acid and/or base binding layer 20.

Figure 4:
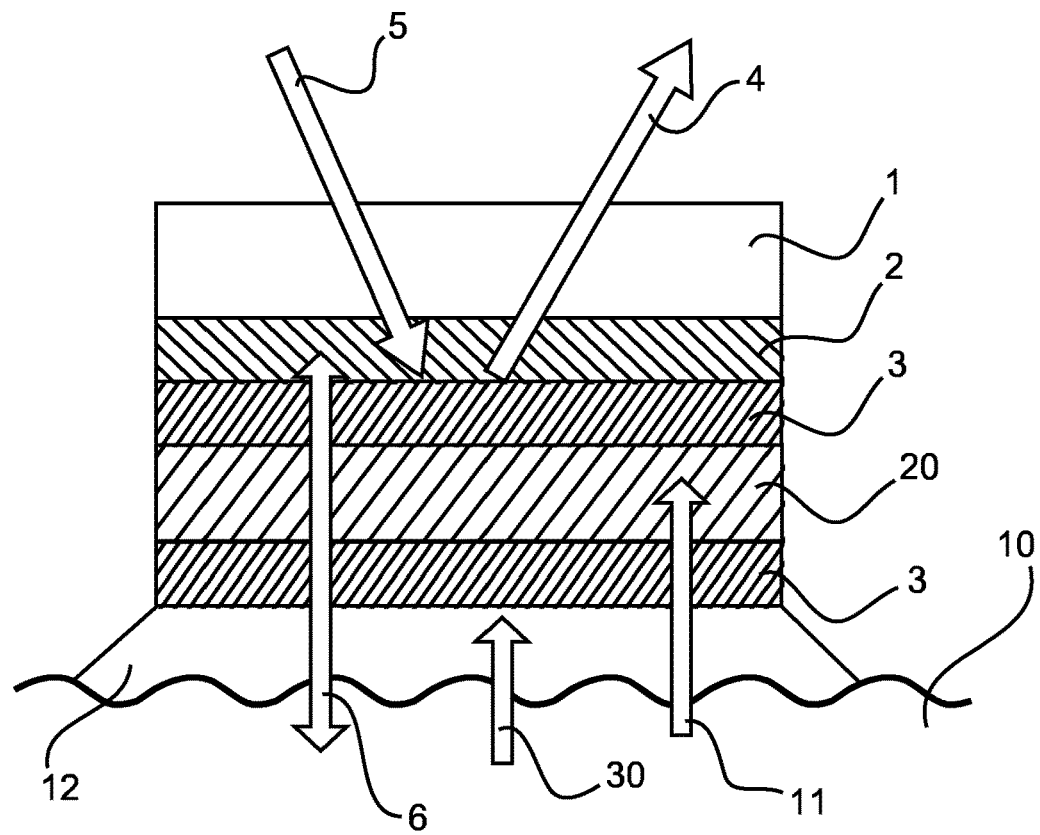
FIG. 4 depicts a further embodiment of the present invention, comprising a chemo-optical sensor with a volatile acid and/or base binding layer and an additional membrane layer which is transparent to gas and prevents ions to travel form the volatile acid binding layer towards the skin, or from the skin towards the upper layers.

In FIG. 4 another embodiment of the chemo-optical sensor according to the present invention is shown. The chemo-optical sensor comprises a sensing layer 2 as defined herein, a first gas-permeable layer 3 adjacent to the sensing layer 2 as defined herein, a volatile acid and/or base binding layer 20 as defined herein, and a second gas-permeable layer 3 as defined herein which is adjacent to the volatile acid and/or base binding layer 20. It is further operated with a contact medium 12 between the sensor unit and the skin 10. The second gas permeable layer 3 may, or in alternative embodiments, may not, comprise an ion balancing means as defined herein. Further, the contact medium 12 may or may not comprise ion-balancing means as defined herein. This may prevent ions 30 from entering the chemo-optical sensor unit. The present invention further envisages variants of this embodiment, which comprise more than one volatile acid and/or base binding layer 20, e.g. a second volatile acid and/or base binding layer 20 between the sensing layer 2 and the gas-permeable layer 3, or which comprise further gas permeable layers 3, e.g. adjacent to an additional volatile acid and/or base binding layer 20. The layer(s) may further be provided in a different thickness with respect to the sensing layer and/or the gas-permeable layer.

Figure 5:
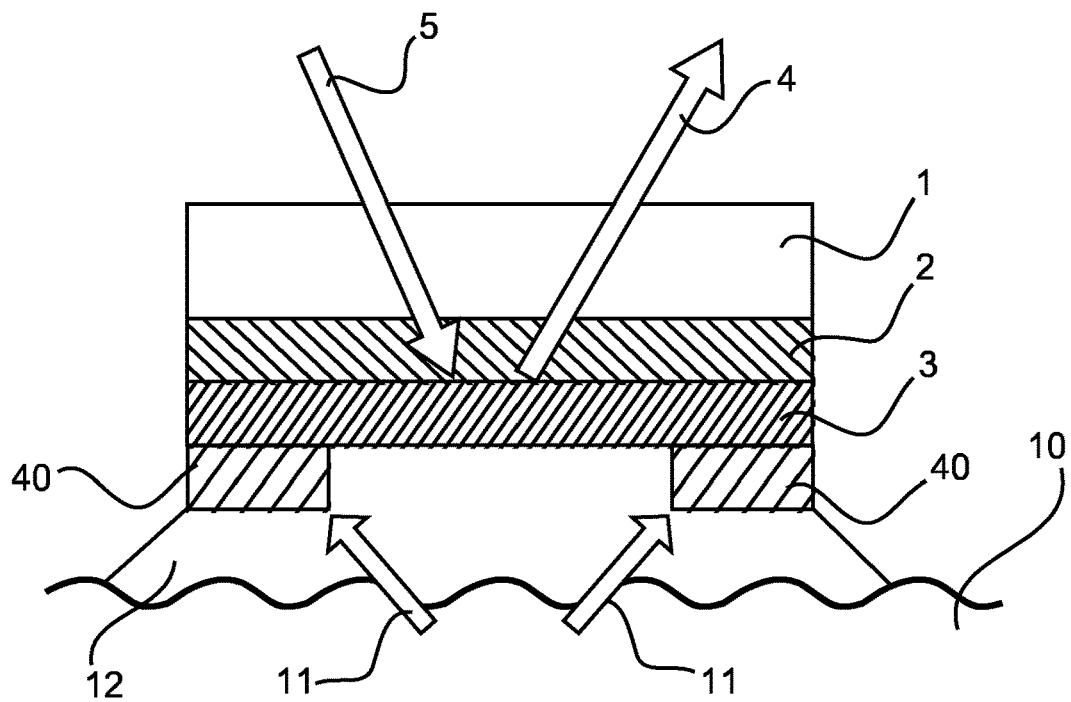
FIG. 5 depicts another embodiment of the present invention, in which blocks of volatile acid and/or base binding layer are followed by gaps.

In FIG. 5 yet another embodiment of the chemo-optical sensor according to the present invention is shown. The chemo-optical sensor comprises a sensing layer 2 as defined herein, a gas-permeable layer 3 adjacent to the sensing layer 2 as defined herein, and a volatile acid and/or base binding layer 20 as defined herein, which has a discontinuous structure 40, i.e. which is formed of blocks of layer followed by gaps. It is further operated with a contact medium between the sensor unit and the skin 10. The contact medium is adapted to fill in the gaps between the blocks of the volatile acid and/or base binding layer 40. The contact medium 12 may or may not comprise ion-balancing means as defined herein. The present invention further envisages variants of this embodiment, which comprise more than one volatile acid and/or base binding layer 20, e.g. a second, continuous volatile acid and/or base binding layer 20 between the sensing layer 2 and the gas-permeable layer 3. The layer(s) may further be provided in a different thickness with respect to the sensing layer 2 and/or the gas-permeable layer 3.

The chemo-optical sensor according to the present invention is suitable for transcutaneous measurement. The chemo-optical sensor unit may, in specific embodiments which are also envisaged, alternatively be used for different measurement purposes, e.g. in the context of microbiological or biotechnological production processes. Preferably, the chemo-optical sensor unit is a transcutaneous sensor unit. The term "transcutaneous sensor unit" as used herein means that the sensor is to be applied or can be applied on the skin. Accordingly, the sensor is capable of measuring blood gas concentrations of a subject via the subject's skin, wherein blood gas may diffuse via the skin into the chemo-optical sensor unit passing a contact medium as defined herein above. The term "blood gas" as used herein refers to gaseous materials present in the blood and capable of exiting a body, which can be measured, e.g. over the skin. The measurement is such that a chemically exact reflection of the gas content of blood is obtainable. The preferred blood gas concentrations to be measured are the concentrations of $O_2$ or $CO_2$, or $O_2$ and $CO_2$. Particularly preferred is the measurement of the concentration of $CO_2$.

In another embodiment of the present invention, the chemo-optical sensor unit as defined herein above may comprise additional components or be combined with additional components.

For example, the chemo-optical sensor may be combined with or comprise at least one light source which is adapted to irradiate the sensing layer as defined herein above. The light source may provide radiation in a predetermined wavelength, preferably light in an excitation wavelength or range of wavelengths adapted to the dye or dyes present in the sensing layer. The light source may have any suitable form, provide any suitable intensity and provide any suitable wavelength(s). The light source may preferably be a light emitting diode (LED).

In a further optional embodiment, the light source may additionally be combined with a light guiding structure. The light guiding structure may be arranged, for example, above the sensing layer/optically transparent layer of the chemo-optical sensor and may be connected to a light source external to the chemo-optical sensor unit, e.g. as defined above. Light from an external light source may be introduced into the light guiding structure, which is adapted to direct said light towards the at least one sensing layer. The light-guiding structure may comprise any suitable light guiding material. Preferably, optical fibers may be used as light guiding material, which may be provided in the form of light-guiding structures. Optical fibers may accordingly be provided as single fibers, or as fiber bundles. A light source, being connected to a light guiding structure, may thus be used to irradiate the sensing layer of a chemo-optical sensor unit according to the present invention, although being located externally. In further embodiments, a light source may be connected to more than one chemo-optical sensor unit via light guiding structures arriving at distinct sensor units.

The chemo-optical sensor may further be combined with a detection device. Such a detection device, for instance a photosensitive device, may be capable of sensing an optical response coming from the sensing layer and may be adapted to generate signals, e.g. electrical signals, corresponding to the sensed optical response. The signals may further be transmitted to an external apparatus for subsequent analysis. The detection device may be adapted to the optical response expected from the sensing layer, e.g. provided by a dye or a combination of dyes as described herein above.

The detection device may further be combined via a light guiding structure to the chemo-optical sensor unit as defined herein. In specific embodiments the same light guiding structure, which provides light from the light source to the sensing layer, may be used to collect the optical response of the sensing layer and to guide said optical response, for instance fluorescent light, via the same or a different optical fiber to a detection device or an apparatus external to the chemo-optical sensor unit for analysis. By using light guiding structures it is thus possible to connect an input and/or output light guiding structure, which is/are coupled to the chemo-optical sensor unit. In this embodiment no additional unit needs to be connected to the chemo-optical sensor unit accommodating the light source and the at least one detection device.

In specific embodiments, the light may thus be transferred into the sensing layer and luminescence, e.g. fluorescence light, may be collected through the same surface of the sensing layer. Alternatively, a light guiding structure connected, for example, via optical fibers to a light source which may be external to the chemo-optical sensor unit, may be used to direct light from an external light source and transmitted through at least one optical fiber towards the at least one sensing layer. At least one detection device, for instance a photosensitive device, may then be included to sense an optical response and may be adapted to generate e.g. electrical signals corresponding to the sensed optical response. Said signals may be transmitted to an external device for analysis. Alternatively, the chemo-optical sensor unit may be adapted to perform said analysis and to output the analysis results to some external device.

Preferably, the at least one light source and the at least one detection device may form a unit. This unit may in a further preferred embodiment be detachably connected to the chemo-optical sensor unit, e.g. by a housing or structure. Accordingly, certain parts of the chemo-optical sensor unit, for instance the sensing layer, gas permeable layer, or a housing and/or supporting structure of the chemo-optical sensor unit may be disposable, whereas other parts of the optical sensor such as the light source and the detection device, or the light guiding structures and may be reused. This reduces costs, since expensive parts such as light sources and/or detection devices and/or electronics do not have to be replaced and can be reused. In specific embodiment, the chemo-optical sensor unit may be composed of two devices or two parts, a disposable or cartridge part and a non-disposable or reusable part. In particular, the disposable or cartridge part may work as passive device and not include any expensive electronics at all. Hence, this part may be manufactured with low effort thereby reducing costs, whereas the second, non-disposable part may include the electronics or optical elements and be reused. It may accordingly also be uses with different disposable parts, e.g. allowing to measure the concentration of different gases (for instance $O_2$ and $CO_2$). Thereby an increased flexibility of the chemo-optical sensor unit can be provided.

Another example of an additional component, which may be combined with the chemo-optical sensor as described above is at least one heating element. Additionally, or alternatively, the chemo-optical sensor may comprise at least one temperature sensor. If, for example, the chemo-optical sensor unit is attached to a person's skin, the heating element may be adapted to increase blood perfusion and gas permeability of the skin, thereby increasing sensitivity and accuracy of the chemo-optical sensor unit, in particular its transcutaneous application. The heating element may be in any suitable form, e.g. could be in the form of a diode or may comprise a thin foil to minimize optical distances and thermal mass. Alternatively, the heating element may be a resistance heater or diode so that the heating element can also be used as a temperature sensor, i.e. heating element and temperature sensor are formed by the same device. This advantageously may reduce costs and space required for installation of a heater and temperature sensor. In further embodiments, the temperature sensor may be realized as a separate element for sensing the temperature of the chemo-optical sensor unit, e.g. in order to avoid injuries or burnings of the skin. During operation the temperature of the heating element and of the contact medium and sensing layer may be increased by the heating element to a temperature in the range of 42° to 45° C. This temperature range may increase capillary blood flow in the skin and bring the capillary blood gas levels close to the arterial blood gas levels. During operation the sensor temperature may accordingly be measured by at least one temperature sensor as defined above, included in the heating element and/or the contact element and/or by a separately provided temperature sensor. The temperature may be controlled such as to have a well defined measurement condition and to prevent burning of the skin.

In further embodiments the chemo-optical sensor unit as define herein may additionally comprise means for thermal insulation of the chemo-optical sensor from its environment and/or an active reduction of a thermal flux into the chemo-optical sensor and/or a reduction of a thermal resistance of the chemo-optical sensor. Accordingly, temperature gradients, for instance in a direction perpendicular and/or parallel to a sensing layer and/or a gas permeable layer included in the chemo-optical sensor, may be minimized or even eliminated, thereby preventing the gradient-dependent signal drift (thermal creep/thermal transpiration). Furthermore, by suppressing temperature gradients, temperature effects on the exited states and chemical balances inside the sensing layer (for instance a dye) may be avoided, and hence, luminescence changes due to temperature may be suppressed. This may further increases reliability and accuracy of the gas concentration measurement.

The means for thermal insulation may at least partially surround the chemo-optical sensor wherein the term "surrounding" may comprise surrounding from any side, but may also comprise surrounding a lateral outer diameter side of the chemo-optical sensor.

In this context a heat conducting means may be present or provided which is at least partially surrounding the chemo-optical sensor and/or the thermal insulation means as defined above. The heat conducting means may surround the chemo-optical sensor at a lateral side thereof. In particular, the chemo-optical sensor could be of disc shape or annular shape, and the heat conducting means could be shaped as a hollow cylinder accommodating said chemo-optical sensor. Moreover, the heat conducting means may be configured to contact a patient's skin in order to apply heat to the skin, thereby increasing blood perfusion and gas-permeability of the skin. The heat conducting means may further be thermally isolated from the chemo-optical sensor by the thermal insulation means as defined above, so that no heat will flow from the heat conducting means into the sensor means, thereby avoiding any temperature effect on the s chemo-optical sensor.

In further specific embodiments, temperature sensors and/or heating elements may be provided as non-disposable or reusable parts of the chemo-optical sensor unit. The temperature sensors and/or heating elements may accordingly be detachably connected to other elements of the chemo-optical sensor unit as defined herein above.

In another aspect the present invention relates to a system for patient monitoring and/or ventilation of a patient, comprising a chemo-optical sensor unit as defined herein above, a ventilation device and/or a monitoring device.

The monitoring device may, for example, include opto-electronics for supplying the chemo-optical sensor unit with light via optical fibers, and for receiving luminescent light from the sensing layer. The monitoring device may further comprise means for determining/calculating a gas concentration based on the received optical response, for instance light intensity of the luminescent light generated in the sensing layer. The monitoring device may further comprise a heater controller for controlling the temperature of the heating element. The heater controller may be adapted for detecting the temperature of the heating element using the temperature sensor included in the chemo-optical sensor unit and for adjusting for instance a current flowing through a resistance heater included in the heating element or the contact element based on the detected temperature. The monitoring device may additionally comprise means for communication with the ventilation device. Said communication means may include at least one communication technique, e.g. wired (cable), wireless (Bluetooth, infrared, RF), etc. In a preferred embodiment, the monitoring device comprises means for calculating/determining the gas concentration, in particular $O_2$ and most preferably $CO_2$, from the measured/sensed optical response of the sensing layer, for instance from the sensed intensity or decay time of the luminescent light. The analyzing device, e.g. monitoring device, may be based on the operation of an algorithm that may also be adapted to compensate, inter alia, for temperature effects for calculating/determining the gas concentration may use.

The ventilation device may include all functions associated of a typical ventilation device for invasive or non-invasive ventilation of a patient with respiratory failure. The ventilation device may, for example, comprise display means and a storage device for displaying and storing information/data received from the monitoring device. In particular, the display means of the ventilation device may be adapted to display a gas concentration, e.g. $O_2$ or $CO_2$, determined by the monitoring device and may further store gas concentration information over a predetermined time period for instance for later evaluation by a physician or for close loop adaptation of the ventilation settings. In another embodiment, the ventilation device may be controlled on the basis of the measured/determined concentration of gas.

In specific embodiments the chemo-optical sensor unit may be operationally coupled to a monitoring device and/or a ventilation device as defined herein above, wherein the monitoring device may be adapted to at least one of analyzing the optical response of the sensing layer, controlling the heating element and/or the temperature sensor, or displaying the determined gas concentrations, etc. The monitoring device or ventilation device may additionally include means for storing monitored data, e.g. as a function of time. These data can be made available at a later time for analysis by a physician, e.g. by transfer to a hospital computer system, or a physician's handheld diagnosis apparatus.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

Solving $CO_2$ Gas in Pure Water

In a first experiment solving $CO_2$ gas in pure water was tested.

Figure 6:
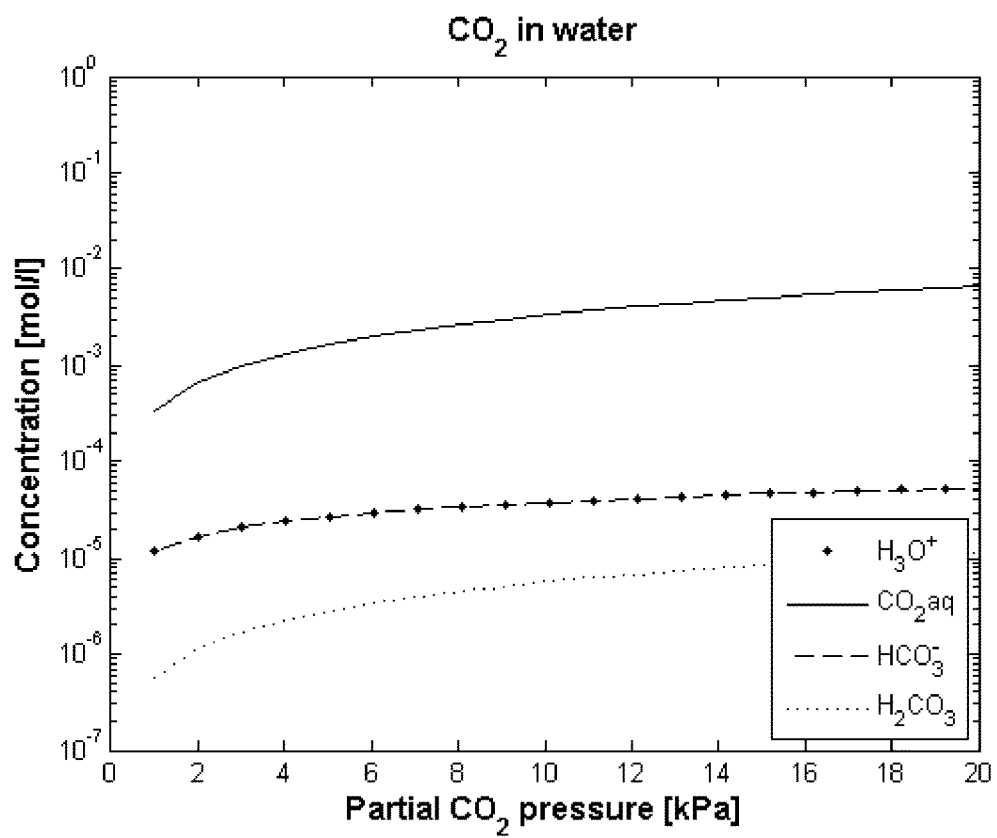
FIG. 6 illustrates the results of dissolving $CO_2$ gas in pure water.

As the ambient partial $CO_2$ pressure rises, the concentrations of the water dissolved components $CO_2aq$, $H_2CO_3$, $HCO_3^-$ and $CO_3^{2-}$ initially rise proportionally. Above ppm levels, the acidity of the water rises, resulting in sqrt dependency for $CO_3^{2-}$ and $H_3O^+$ ions, and the $CO_3^{2-}$ ion concentration stabilizes at a very low level. At the concentration range relevant for transcutaneous measurements, indicated with bullets, the total amount of dissolved $CO_2$ components is dominated by $CO_2aq$, and almost equal to the amount of $CO_2gas$ in air (see FIG. 6).

Example 2

Solving $CO_2$ Gas in a Standard Phosphate Buffer

In a second experiment solving $CO_2$ gas in a standard phosphate buffer was tested.

Figure 7:
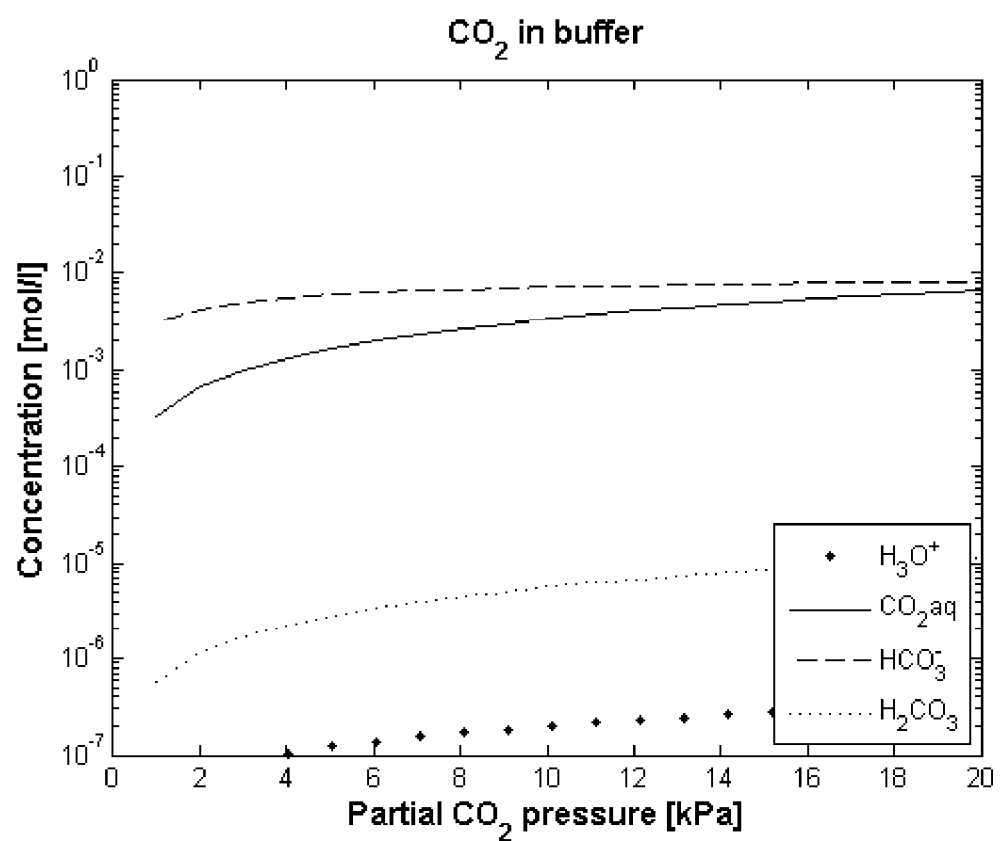
FIG. 7 depicts the results of dissolving $CO_2$ gas in a standard phosphate buffer.

The buffer stabilizes acidity and will absorb volatile acidic components that may enter the system. Due to the stabilized acidity, also the proportionality of water dissolved ions concentrations continues up to higher ambient partial $CO_2$ pressures. At the concentration range relevant for transcutaneous measurements, indicated with bullets, the total amount of dissolved $CO_2$ components is dominated by $HCO_3^-$ ions, and roughly an order of magnitude higher than the amount of $CO_2$ gas in air. In a system with slow gas permeation, this additional $CO_2$ buffering can cause slower response times (see FIG. 7).

Example 3

Solving $CO_2$ Gas in a Diluted Phosphate Buffer

In a third experiment solving $CO_2$ gas in a diluted phosphate buffer was tested.

Figure 8:
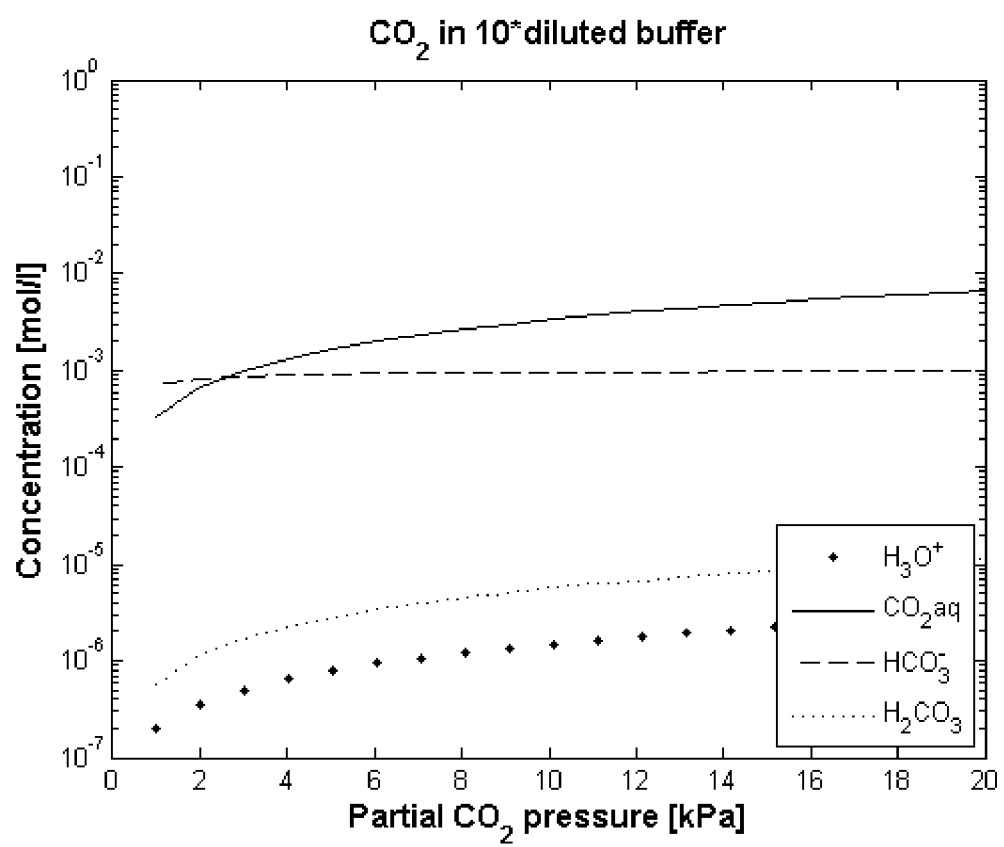
FIG. 8 shows the results of dissolving $CO_2$ gas in a diluted phosphate buffer.

The buffer stabilizes acidity and will absorb volatile acidic components that may enter the system. But in this case the acidity already starts to rise below the concentration range relevant for transcutaneous measurements, indicated with bullets. In this case the total amount of dissolved $CO_2$ components in the range of interest is still dominated by $CO_2$aq, so even in a system with slow gas permeation there will not be a penalty in response times (see FIG. 8).

The invention claimed is:

1. A chemo-optical sensor unit for transcutaneous measurement of a concentration of a gas, comprising:
   at least one gas-permeable sensing layer adapted to be irradiated with a predetermined radiation; and
   at least a first gas-permeable layer adjacent to one side of the at least one sensing layer, adapted to pass gas whose concentration is to be measured through the gas-permeable layer towards the sensing layer;
   wherein said chemo-optical sensor unit is adapted to operate with a contact medium between the chemo-optical sensor unit and the skin and wherein the chemo-optical sensor unit is adapted to measure an optical response of the at least one sensing layer whose optical response depends on the concentration of the gas;
   characterized in that the chemo-optical sensor unit further comprises at least one volatile acid and/or base binding layer adapted to pass gas whose concentration is to be measured through the volatile acid and/or base binding layer towards the sensing layer, wherein the at least one volatile acid and/or base binding layer is an additional layer located in the gas-pathway from the skin to the sensing layer.

2. The chemo-optical sensor unit of claim 1, wherein said at least one volatile acid and/or base binding layer comprises at least one compound capable of immobilizing said volatile acid(s) or volatile base(s) or of converting said volatile acid(s) or volatile base(s) into non-volatile molecules and/or of converting said volatile acid(s) into less acidic volatile molecules, and/or said volatile base(s) into less alkaline molecules.

3. The chemo-optical sensor unit of claim 1, wherein said at least one volatile acid and/or base binding layer has a non-continuous structure allowing the contact medium to directly contact the at least one gas-permeable layer at one or more positions.

4. The chemo-optical sensor unit of claim 3, wherein said non-continuous structure is a single or multiple sequence of blocks of volatile acid and/or base binding layer followed by single or multiple gaps.

5. The chemo-optical sensor unit of claim 1, additionally comprising at least a further, second gas-permeable layer adjacent to one side of the at least one volatile acid and/or base binding layer or to one side of the first gas-permeable layer, adapted to pass gas whose concentration is to be measured towards the sensing layer and further adapted to prevent ions to pass from the chemo-optical sensor unit to the skin, or from the skin into the chemo-optical sensor unit.

6. The chemo-optical sensor unit of claim 5, wherein said further, second gas-permeable layer comprises an ion-balancing means capable of removing the ions associated with volatile acids and/or bases.

7. A chemo-optical sensor unit with a contact medium, comprising:
   a chemo-optical sensor unit according to claim 5, and
     a contact medium, the contact medium being provided at the interface between the chemo-optical sensor unit and the surface layer on which the measurement of gas is to be carried out,
     wherein the contact medium comprises an ion-balancing means capable of removing the ions associated with volatile acids and/or bases.

8. The chemo-optical sensor unit with the contact medium of claim 7, wherein said ion-balancing means is an ion-trapping means, an ion-exchange polymer, an ion-exchange resin, an anion-exchange resin or any combination thereof.

9. The chemo-optical sensor unit of claim 2, wherein said at least one compound capable of binding or converting a volatile acid or volatile base is a chemical buffer comprising a phosphate buffer.

10. The chemo-optical sensor unit of claim 1, wherein said at least one volatile acid and/or base binding layer has a thickness of about 10% to about 300% of the thickness of the at least one sensing layer or of the at least one gas-permeable layer.

11. The chemo-optical sensor unit of claim 1, wherein said at least one gas-permeable layer and/or said at least one sensing layer and/or said at least one volatile acid and/or base binding layer comprises a silicon rubber.

12. The chemo-optical sensor of claim 1, wherein said at least one sensing layer and optionally said volatile acid and/or base binding layer comprises luminescent material and wherein said first gas-permeable layer is adapted to prevent light from passing through the gas-permeable layer.

13. The chemo-optical sensor of claim 1, wherein said chemo-optical sensor is a transcutaneous sensor unit for measuring blood gas concentration, comprising gas concentrations of $O_2$ or $CO_2$ or simultaneously $O_2$ and $CO_2$.

14. The chemo-optical sensor unit of claim 1, further comprising: at least one light source adapted to irradiate the sensing layer, and optionally a light guiding structure connected to the light source; and at least one detection device adapted to detect the optical response of the sensing layer, and optionally a light guiding structure connected to the detection device, wherein at least one of the light source, light guiding structure and/or the detection device are detachably connected to the chemo-optical sensor unit.

15. A system for patient monitoring and/or ventilation of a patient, comprising a chemo-optical sensor unit as defined in claim 1, a ventilation device and/or a monitoring device.

* * * * *